United States Patent

De La Huerga

[19]

[11] Patent Number: 6,139,495
[45] Date of Patent: Oct. 31, 2000

[54] MEDICAL ACCIDENT AVOIDANCE METHOD AND SYSTEM

[76] Inventor: Carlos De La Huerga, 9190 N. Upper River Rd., Milwaukee, Wis. 53217

[21] Appl. No.: 09/067,394

[22] Filed: Apr. 28, 1998

[51] Int. Cl.[7] .................................................. A61B 5/00
[52] U.S. Cl. .......................... 600/300; 600/301; 128/903; 128/904
[58] Field of Search ..................... 235/375, 462; 705/3; 283/67; 600/300; 128/904, 903

[56] References Cited

U.S. PATENT DOCUMENTS

| | | | |
|---|---|---|---|
| 4,476,381 | 10/1984 | Rubin | 235/375 |
| 4,730,849 | 3/1988 | Siegel | 283/70 |
| 4,732,411 | 3/1988 | Siegel | 283/75 |
| 4,835,372 | 5/1989 | Gombrich et al. | 235/375 |
| 4,857,713 | 8/1989 | Brown | 705/3 |
| 4,857,716 | 8/1989 | Gombrich et al. | 235/462 |
| 4,916,441 | 4/1990 | Gombrich | 340/712 |
| 5,071,168 | 12/1991 | Shamos | 283/117 |
| 5,272,318 | 12/1993 | Gorman | 235/375 |
| 5,381,487 | 1/1995 | Shamos | 382/2 |
| 5,401,059 | 3/1995 | Ferrario | 283/67 |
| 5,659,741 | 8/1997 | Eberhardt | 395/615 |
| 5,660,176 | 8/1997 | Iliff | 128/630 |
| 5,732,401 | 3/1998 | Conway | 705/3 |
| 5,868,669 | 2/1999 | Iliff | 600/300 |

*Primary Examiner*—Cary O'Connor
*Assistant Examiner*—Michael Astorino
*Attorney, Agent, or Firm*—Quarles & Brady, LLP

[57] ABSTRACT

A method and system for identifying medical events which have not been prescribed for performance on a patient prior to performing the events which includes specifying a specified event to be performed on the patient, comparing the specified event to a valid event set indicating events which have been prescribed for the patient and, where the specified event is not a valid event, indicating that the specified event is not a valid event. In addition, where an event is not a valid event, the system may disable a medical apparatus from performing the event so as to ensure that invalid events are not performed and, where a valid event is performed, the system may update the valid event set to reflect performance. Also, the system can be used to perform a check of diagnosis and prescription.

40 Claims, 10 Drawing Sheets

MEDICAL ACCIDENT AVOIDANCE METHOD AND SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to electronic information tracking methods for use in the medical field and more particularly to a method and system for tracking, verifying and automatically updating medical procedures performed on patients.

For the purposes of this explanation, any medical procedure, diagnostic procedure, therapeutic procedure or administration of medicine will be referred to hereinafter as a medical event and any event prescribed by a physician will be referred to as a prescribed event. In addition, hereinafter, unless used in conjunction with diagnosing a medical problem or prescribing a treatment for a medical problem, where the term "physician" is used, any other term (e.g. nurse, physicians assistant, facility personnel, etc.) used to identify a person working at a health care facility to perform or administer a medical event could be substituted.

Clearly, one of the most important concerns for any medical facility is that medical events be correctly prescribed. In the case of a medicine, this means that given a set of factors including prior medical history (e.g. medical and diagnostic procedures, currently ingested medicines, past addictions, etc.), current conditions (e.g. age, allergies, addictions, etc.) and current symptoms, the correct medicine be chosen for administration at the correct time. In the case of a procedure, this means that, given the factors identified above, the correct procedure be chosen for performance at the correct time.

To ensure that correct procedures and medications are prescribed, only trained physicians (and in some cases physician assistants) are allowed to prescribe all but the least invasive medical events. It is assumed that medical training of these individuals is sufficient to essentially eliminate the possibility of incorrect diagnosis and mis-prescription.

Years ago correct diagnosis and a suitable prescription of medical events were relatively simple as the number of known medical problems, their symptoms and suitable cures were limited. Diagnosis and prescription were also made easier by the fact that often a doctor would treat a patient throughout the patient's life and thus had an intimate knowledge about the patient's medical history, allergies, etc.

However, in today's medical environment, proper diagnosis and suitable prescription of medicine and procedures is a much more arduous task for many reasons. First, only very rarely will a person have a single doctor throughout most or his or her life. People often relocate to different areas within the country for various reasons. In addition, many physicians relocate during the course of a career making it difficult to maintain physician-patient relationships. Moreover, even where neither a patient nor a physician physically relocates, a patient may be forced to change physicians for other reasons such as a change in insurance or a job change. Furthermore, many doctors specialize in only one area of medicine and therefore patients are often treated by many different doctors to address different symptoms. In these cases, physicians are no longer intimately aware of medical histories and correct diagnosis is therefore more difficult.

Second, literally hundreds of patients are examined and treated on a daily basis in large modern medical facilities, each doctor or nurse interacting with as many as twenty or more patients within a single day. With such high traffic it is very rare for a physician to delve deeply into a patient's medical history to identify other than a handful of symptoms prior to diagnosis and prescription of a treatment. While many diagnosis and prescriptions which are based on the handful of known symptoms might be correct despite medical histories, it is clearly possible that some of the diagnosis and prescriptions might be incorrect in light of medical histories including allergies, addictions, previous medical events, etc.

Third, modern research has lead to the discovery of a plethora of previously unknown medical conditions and medical problems, a huge number of known symptoms for each condition or problem and in some cases, a large number of different possible cures, each of which might have several different side effects and each of which interact with other medicines and procedures in different manners. Given this minefield of considerations, it is now more difficult than ever to diagnose problems and prescribe correct medicines and procedures.

Tools have been developed to help physicians diagnose problems and prescribe correct medicines and procedures. For example, reference books which list, among other things, symptoms, cures, side effects and how a cure will interact with other types of medicines and procedures can be consulted prior to diagnosis and prescription. This same information has also been provided in computer searchable form accessible by a physician or a nurse to aid diagnosis and prescription. An example of a computer aided diagnostic system which could be used by a physician or could also be used by a patient is described in U.S. Pat. No. 5,660,176 entitled Computerized Medical Diagnostic And Treatment Advice System which issued on Aug. 26, 1997. While reference books and computers can be useful diagnostic and prescription tools when employed, these tools are seldom used for a number of reasons.

First, because most doctors have to examine many (e.g. 20 or more) patients each day, doctors only have a short time (e.g. 15 to 20 minutes) with each patient. During this time, a doctor usually only identifies a handful (e.g. 3 to 5) of symptoms and then prescribes a treatment. Simply put, time does not allow most physicians to consult an external information source.

Second, psychologically many patients are uncomfortable with a physician who consults a reference to diagnose a condition and prescribe a treatment. Such consultation can be construed as a sign of inexperience. For this reason, many doctors are uncomfortable accessing a reference in front of a patient and therefore will not access a reference except for in extremely complex cases.

After a problem has been diagnosed and one or more medical events have been prescribed, another extremely important concern for any medical facility is that the correct medical event be performed. If incorrect events are performed, a patient's condition can further deteriorate and, in some cases, can lead to a patient's premature demise.

For example, injury can result from over medication where a prescribed medicine is administered in an unprescribed excessive dose or if a prescribed dose is administered twice, once by a first physician and second by another physician unaware of the first administration. Also, if a physician elects not to administer a dose of prescribed medicine under the erroneous belief that another physician at a facility has already administered the prescribed dose, under medication results which can cause patient discomfort and condition deterioration.

Injury and/or discomfort can result where medicine is administered too soon after a medical procedure or a procedure is performed to soon after a medicine has been administered. Also, injury can result where several procedures are performed within a short time period. For example, excessive radiation from consecutive diagnostic or therapeutic procedures within a short time period can cause illness.

As with diagnosis and prescription, the task of performing prescribed medical events at prescribed times has become relatively difficult in the modern medical environment. Years ago physicians dealt with a relatively small number of patients, medicines and procedures on a daily basis and therefore it was easier to track medical event performance.

Today, each physician interacts with a relatively large number of patients, medicines and procedures on a daily basis and tracking medical event performance is extremely difficult and time consuming. The task of tracking event performance is exacerbated by the fact that many medical facilities are expansive including specialized departments which are spread out throughout the facility, many departments being on different floors or even in different buildings. For example, diagnostic examination, imaging, surgery, recovery, etc., areas are all usually separate and staffed by different personnel. As a patient is moved from one department to another event performance might be delayed or even missed.

In addition, many patients are admitted into a medical facility for a period which is longer than a single shift. Where facility personnel changes during a patient's stay, physicians on the later shift might not be able to determine if a medical event was performed during the earlier shift.

Most medical facilities enforce rigid guidelines designed to ensure that unprescribed medical events are not performed and to ensure that performed events are documented. For years the standard for identifying prescribed events and for determining if an event has been performed has been to provide a clip board which is hooked to a patients bed. Typically the board is updated manually by a physician each time an event is performed. Prior to performing any medical event, a physician examines the board to make sure that the event was prescribed and to identify prescribed treatment time. If the event is required at the present time, the physician performs the event and updates the board to reflect performance.

Unfortunately, despite regulations, sometimes a physician forgets to examine a board prior to performing event. Similarly, sometimes a physician forgets to update a board after performing an event or, may make a mistake in updating the board. In addition, even if updated correctly, a physician on a later shift may not be able to decipher information on a board and may therefore erroneously reperform an event or fail to perform a prescribed event. Moreover, there is always the possibility that two boards may accidentally be interchanged such that an event could be performed on the wrong patient.

One other problem with existing methods for diagnosis, prescription, performance of prescribed treatment and treatment tracking is that diagnosis and prescription may often be modified during a patient's stay at a facility and the modification might not always take into account a patient's complete medical history. For example, a patient might be admitted to a hospital for a five day period. During the period, the patient might initially be diagnosed with sickness ZZZ for which drug C is typically prescribed. However, because of allergies which prevent the use of drug C, drugs A and B might be administered and recorded on the board without identifying the allergy. On the third day the diagnosed sickness might be changed from ZZZ to YYY and a procedure P might be performed to treat sickness YYY wherein procedure P is typically followed up by administration of drug C to counteract side effects of treatment P. Assuming the allergy is not indicated on the board, a nurse might automatically administer drug C which would cause the patient to have an allergic reaction. While this example is simplistic, it is helpful to illustrate the type of problem which can result from present manual diagnosis, prescription, administration and tracking procedures. This problem is exacerbated during longer hospitalization periods and as different treatments are prescribed.

To ensure that medical events are not prescribed which might adversely interact with factors in a patient's medical history (e.g. allergies, additions, etc.), it is policy at most medical facilities that only a single primary physician who is most knowledgeable about the patient's medical history prescribe medical events during the patient's stay at the facility. Thus, in the example above, presumably the physician who initially prescribed drugs A and B would remember the patient's allergy to drug C and would not prescribe drug C after procedure P.

While this "primary physician" policy is helpful, this policy can lead to some undesirable situations. For example, if a new symptom or condition occurs and the primary physician is unavailable, one of two choices has to be made. First, an attending physician may elect to wait until the primary physician can be contacted to determine how to respond to the new condition or symptom. Clearly this choice causes delay in treatment and may exacerbate the patient's condition. In addition, assuming the primary physician is located, the primary physician might not remember all aspects of the patient's medical history which may have some bearing on which medical event to prescribe to treat the symptom or condition.

Second, the attending physician may use what little medical history information is available on the patient's board to prescribe a medical event to treat the new condition or symptom. Neither of these two options is optimal as each option has several obvious pitfalls.

Thus, it would be advantageous to have a system which could automatically double check patient diagnosis and event prescription as a function of medical history, automatically track event performance, identify unprescribed events prior to performance and stop performance of unprescribed events. In addition, it would be advantageous if, when a diagnosis or prescription is seemingly incorrect, an apparatus could indicate an incorrect diagnosis or prescription.

BRIEF SUMMARY OF THE INVENTION

The present invention includes a system which, prior to performing a medical event, automatically checks a patient medical record to identify if the event was prescribed and, where the event was not prescribed, indicates that the event was not prescribed. For the purposes of this explanation prescribed events will be referred to as valid events and events which were not prescribed will be referred to as invalid events.

According to the present invention, a system is provided which includes an identification device associated with a first patient, the identification device including a power source, a memory and a transponder linked to the source for power and linked to the memory to read data stored in the memory, at least one specifying device including a power source and a transponder linked to the source for power, the specifying device specifying a procedure to be performed on a patient, the procedure being a specified event, each of the identification and specifying devices being system devices. A first system device transponder includes a transmitter and a second system device transponder includes a receiver, one of the system devices includes an indicator, one of the system devices is a comparison device including a memory and a processor linked to the comparison device memory, the memory of the comparison device including a patient specific valid events section which includes a list of all valid events which have been prescribed for the first patient and may be performed on the first patient.

To initiate an identification process, the transmitter transmits an initial signal which is received by the receiver and, after the initial signal is received and during the identification process, the comparison device processor compares the specified event to the valid events which may be performed on the associated patient. When the specified event is not a valid event, the comparison device processor causes the indicator to indicate that the specified event is an invalid event.

A primary object of the invention is to identify medical events which are not prescribed prior to performing the events. Once an event which has not been prescribed is identified, a physician can determine if the event should be performed. In this manner, if an event is invalid (i.e. was not prescribed), either the event can be avoided or, if necessary, the event can be performed after an independent medical judgement is made that the event is required.

In one embodiment, the specifying device is the first device and the identification device is the comparison device. In this case, all valid events are stored in the valid events section of the identification device which is with the patient at all times. To determine if a specified event is a prescribed event in this case, the specifying device transmits (via RF or the like) a message which is received by the comparison device, the message specifying the event to be performed. When the message is received, the comparison device compares the specified event to the valid events and, where the specified event is invalid, indicates so.

In another embodiment the first device is the identifying device and the specifying device is the comparison device. In this case, to determine if a specified event is a prescribed event, the identifying device transmits a message identifying the patient, the message received by the specifying device. When the message is received, the specifying device compares the specified event to the valid events and, where the specified event is invalid, indicates so.

In yet another embodiment the identification device is the comparison device and each of the identifying and specifying devices might be equipped with a receiver and a transmitter. To identify an invalid event, the specifying device transmits a message indicating a specified event, the comparison device receives the message and compares the specified event to the valid events and, where an invalid event is identified, the comparison device transmits a message to the specifying device indicating invalidity. When the invalid message is received, the specifying device indicates invalidity.

In one aspect the inventive system is used with a medical apparatus for performing a specified event, one of the system devices is an updating device which communicates with the medical apparatus. In this case the system is also for identifying an updated set of valid events after a specified event has been performed and modifying the valid events to reflect the updated set. After an event has been performed, the updating device determines that the event has been performed and modifies the valid events to reflect performance of the specified event. For example, a patient might be on a daily drug routine including administration of drug A every six hours. However, drug A may cause adverse reactions in a patient within twenty-four hours after irradiation of a tumor. Assuming irradiation is prescribed and performed, after performance of the irradiation, the updating device updates the prescribed events to indicate performance of irradiation. In addition, the updating device can update the valid events set to reflect that administration of drug A is not a valid event for the next twenty-four hours after the irradiation. To this end, the processor may have access to a modifier rule set including modifier rules which identify how to modify a valid event set as a function of several different factors including a performed prescribed event.

Thus, another object of the invention is to automatically track performance of prescribed and non-prescribed events as they are performed. This feature eliminates the need for a physician to manually indicate event performance. In addition, this feature eliminates the possibility that a physician might incorrectly indicate event performance or that a physician on a later shift might not be able to decipher an earlier physician's event performance indication. Moreover, this feature, in conjunction with the invalid event indicating feature identified above, renders it nearly impossible to double medicate a patient or perform two unintended identical procedures on a patient. This is because, after an event has been performed once, unless represcribed, attempting to perform the event a second time would cause an invalid event indication.

One other object is to automatically modify a valid event set as a function of performed events, in effect offering a new prescription in light of recent changes in medical history (i.e. performance of the prescribed event). To this end, the modifier rule set allows the updating device to, not only indicate that a specific event has been performed, but to take into account performance of the event and a patient's detailed medical history to update the valid event set. Thus, after an event is performed, the updating device may render previously valid events invalid for a specific time period or for an indefinite period if the previously valid event would likely cause adverse effects in light of the performed event.

In this regard, according to one other aspect of the invention, instead of automatically modifying a valid event set as function of the modifier rule set and medical history (including a recently performed medical event), the updating device may perform a process applying the modifier rule set to the medical history to identify modifications which likely should be made to the valid event set and can then indicate the likely modifications to a physician via a display or the like at which point the physician can determine whether or not to accept the modifications. If the physician accepts the modifications the valid event set is updated. However, if the physician does not accept the modifications the valid event set is not updated.

In another aspect, every medical apparatus used to perform a medical event might include a specifying device which can disable the medical apparatus if an invalid event is identified. For example, it is contemplated that a radiation therapy machine would include a specifying device which can disable the machine if an invalid therapy session is specified.

Thus, another object of the invention is, in addition to indicating an invalid event, disabling invalid events until an independent and addition medical judgement is made that the event is required. If the event is required, a physician can override the specifying device and perform the event.

In one aspect the identification device also includes a fastener configured to attach the identification device to the patient. Preferably, the fastener includes a band (e.g. wrist band) which can be secured around a patient's limb.

One other object of the invention is to maintain a complete valid events set and a complete medical history with each patient in a medical facility at all times. To this end, by fastening an identification device to each patient at a facility which is never removed during the patient's stay at the facility, any physician can access the patient's valid events set for any purpose.

In another aspect, an indicator can indicate invalid events and valid events and, when a specified event is a valid event, the indicator specifies a valid event. Preferably, valid events include a first subset of valid events being prescribed events to be performed within a present time period and a second subset of valid events being prescribed events to be performed within a time period other than the present period. In this case, the interrogator preferably separates the valid events into first subset events and second subset events and compares the specified event to events in each of the unprohibited, first subset and second subset events and then indicates if an event is a first subset or a second subset event.

One other object is to provide a system which clearly indicates events which should not be performed, indicates events to be performed at some time and indicates other events which are prescribed and to be presently performed. This feature helps physicians perform events in a timely fashion. The invention also includes a method to be used with the above described system.

In addition to identifying events which were not prescribed prior to performing the events and tracking events as they are performed, the present invention also contemplates a system for independently and automatically checking to determine if, given a patient's complete medical history and current symptoms, a diagnosis is likely correct and, if the diagnosis is likely correct, if a prescribed medical event is suitable to treat the diagnosed problem in light of the patient's medical history.

To this end, the invention contemplates a system wherein, prior to diagnosis, when a patient is admitted to a medical facility, a medical history record is formed and stored in a medical history section of an electronically accessible memory. The history includes age, weight, height, allergies, previous medication and medical procedural history, present medication taken, present prescribed medicines, addictions, past symptoms, current symptoms, dietary constraints, etc. While an entire medical history can be entered manually, preferably a medical history device can be used to download a patient's medical history into the history section. One such medical history device (i.e. a card) is described in U.S. Pat. No. 5,659,741 which is entitled Computer System And Method For Storing Medical Histories Using A Carrying Size Card which issues on Aug. 19, 1997 and which is incorporated herein by reference. In the alternative, it is contemplated that eventually all medical histories will be accessible by authorized medical personnel via the Internet very shortly. In this case, when a patient is admitted, the patient's history is simply be downloaded into the history section.

After the complete medical history is loaded onto the history section, when the patient is examined, a physician accounts for all known symptoms and diagnoses a problem. As is typical, the known symptoms likely only include a handful of symptoms. In addition to diagnosing the problem, the physician also prescribes one or more medical events to be performed to eliminate the problem. The symptoms, are entered into the history section and become a part of the patient's medical history. The diagnosis and prescribed events are stored in a random access memory for manipulation.

After the symptoms, diagnosis and prescribed event have been entered, a processor reads the diagnosis and performs a diagnosis check to independently determine, given the complete medical history of the patient and the patient's current symptoms, if the diagnosis could be accurate and, if so, if the diagnosis is the most accurate. If the diagnosis is completely inaccurate, the processor indicates that the diagnosis is likely inaccurate and thereafter requires a second independent medical judgement by the initial physician or another physician that the diagnosis is warranted.

If the diagnosis could be accurate but is likely not the most accurate diagnosis, the processor indicates that the diagnosis might be accurate but that another diagnosis might be more accurate and can then indicate the diagnosis which is likely more accurate. In the alternative, the processor could simply accept the diagnosis although it might not be the most accurate. To this end, the processor applies a diagnostic rule set (DRS) to the patient's medical history (including current symptoms) to generate a possible correct diagnosis set (PCDS). Then the processor compares the diagnosis to the PCDS to determine if the diagnosis is correct or likely incorrect. After a correct diagnosis is entered or a physician accepts a likely incorrect diagnosis, the diagnosis is stored as part of the patient's medical history. After the diagnosis is stored the processor next considers the prudence of the prescribed events.

To this end, the processor applies a prescriptive rule set (PRS) to the patient's medical history (including current symptoms and the recently stored diagnosis) to generate a possible correct prescription set (PCPS). Then the process compares the prescription to the PCPS to determine if the prescription is correct or likely incorrect. If the prescription is completely inaccurate, the processor indicates that the prescription is likely inaccurate and therefore requires a second independent medical judgement that the prescription should be prescribed.

If the prescription is accurate or the physician accepts a likely inaccurate prescription the process stores the prescription in the patient's medical history. In addition, the processor also stores the prescription in the valid event set for the patient.

An example of how the processor might operate to screen a prescribed event is instructive. Given a diagnosis, any of several different prescribed events might be advantageous, depending on an individuals complete medical history. For example, a patient might be allergic to drug A and therefore, although drug A might be suitable in most cases for treating sickness ZZZ, a drug B which the patient is not allergic to and which is also suitable to treat ZZZ is a better prescribed event. In this case, if a physician failed to account for the patient's allergy and prescribed drug A, the processor would recognize that drug A should not be prescribed. Here, the processor first rejects the prescribed event indicating that the event is probably incorrect. In addition, the processor might indicate why the prescription is probably incorrect. In the example above, the device indicates that the allergy renders the prescription unsuitable.

In this manner, although a physician still makes an initial diagnosis and prescribes a medical event to treat a diagnosed condition without consulting an independent source and therefore no additional time is required to perform a diagnosis and prescribe the event, the inventive system automatically checks the diagnosis and prescribed event to ensure that a blatant error does not occur. Where no error is detected, prescribed events are added to the valid events set associated with the patient.

Yet another advantage of the present invention is that new ailments can be added to the DRS thereby notifying each physician to consider different, new and/or unusual diagnosis when symptoms are encountered. While a physician can elect to ignore the PCDS, at least the physician is aware of the possibility. In addition, new prescriptions can be brought to the physician's attention for treating diagnosis. This is important as, for many diagnosis, there may be several different possible remedies, some of which have been developed in relative obscurity. The overall result is more accurate diagnosis and more suitable prescription.

One other advantage to the present invention is that any attending physician can change a diagnosis and prescribed events in the absence of a primary physician when a new symptom or condition occurs. This is because the system checks all specified events against the backdrop of the patient's detailed medical history and other current symptoms to ensure that the attending physician does not prescribe an event likely to further injure the patient.

One other object of the invention is to provide a complete log of all diagnosis and prescriptions and medical events performed on a patient, including information indicating the physician who diagnosed, prescribed or performed. To this end, every time a device is used for diagnosis, prescription or performing an event, the device may require physician identification which can be stored in the patient's medical history.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVENTION

Figure 1:
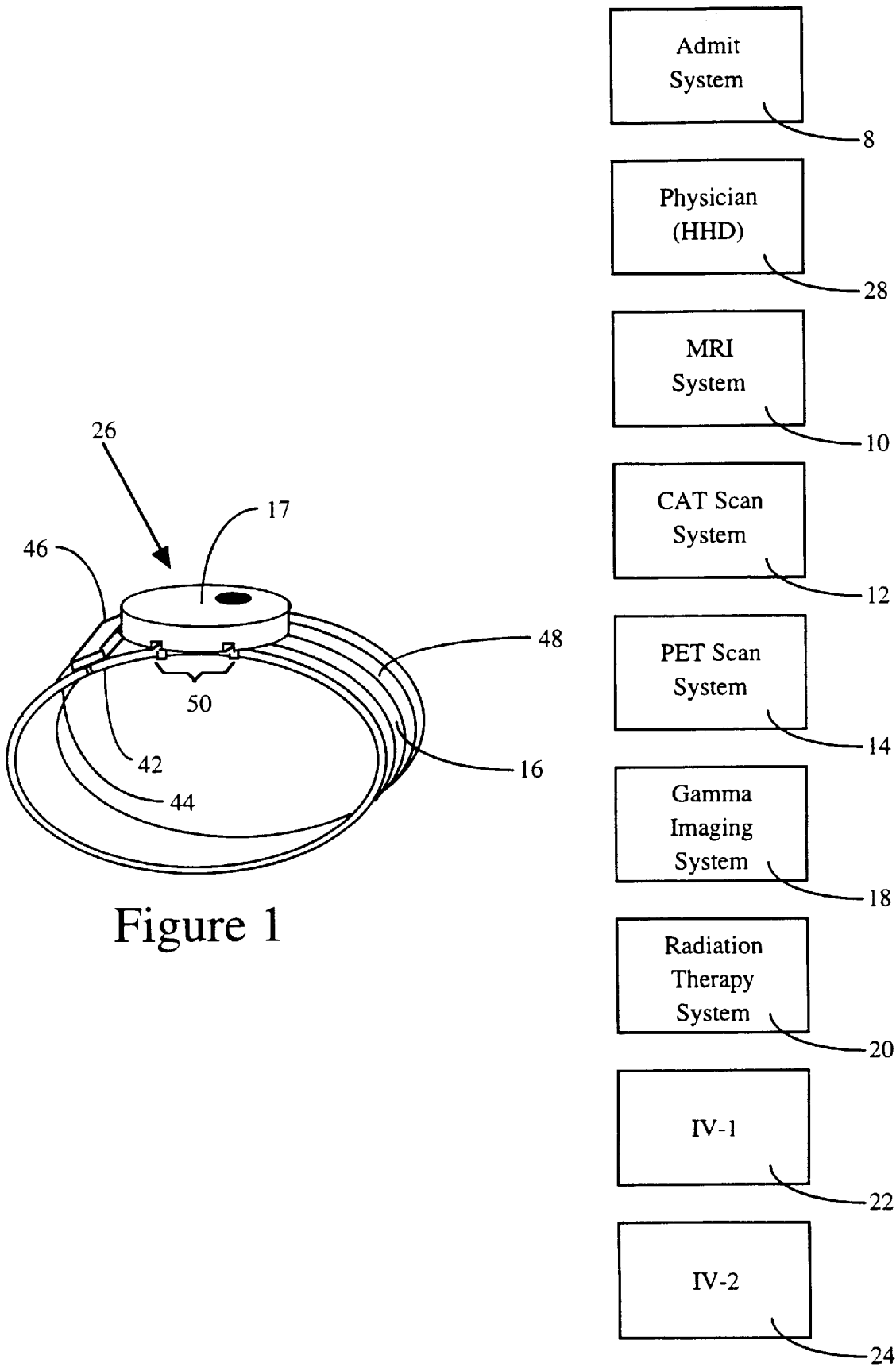
FIG. 1 is a schematic diagram illustrating various system components which together form the inventive accident prevention system.

Referring now to the drawings wherein like reference characters, numbers and symbols represent like components and signals throughout the several views and referring in particular to FIG. 1, the present invention will be described in the context of a typical medical facility environment. When a patient is admitted into a hospital, upon arrival patient information is taken from the patient using an admit system 8. Information received from the patient typically includes the patient's name, age, date of birth, insurance carrier, perhaps some patient medical history, current symptoms and so forth. During admittance, each patient is typically provided with a plastic bracelet around his wrist which often includes only tertiary information for identifying a patient.

After being admitted the patient is examined by a physician. The physician identifies current symptoms and, in light of a brief medical history usually orally related by the patient, diagnoses a likely ailment and issues a prescription. Thereafter, one or several different machines for performing medical, diagnostic or therapeutic events (i.e. processes) used to either treat the patient or further diagnose the ailment. These machines or apparatuses might include an MRI machine 10, a CAT scan machine 12, a PET scan machine 14, a gamma imaging apparatus 18, a radiation therapy apparatus 20, a first IV system 22, a second IV system 24 and so on. While this list is not meant to be exhaustive it should be clear that there are a huge number of different machine related events which are performed at a typical medical facility.

According to the present invention, a streamlined and yet more complete admit system 8 used in conjunction with an electronic identification device generally referred to by numeral 26, a physician's hand held programming device (HHD) 28 and "smart" machines 10, 12, 14,16, 18, 20, 22 and 24 facilitate automatic checking of physician diagnosis and prescription, automatic identification of medical events which were not prescribed prior to performance and automatic updating of a patient's medical history after an event has been performed.

In order to simplify this explanation a first preferred system will be described in detail and thereafter other preferred systems and modifications to the first preferred system will be described. With respect to the first preferred system, that system will be divided into four separate sub-systems, portions of the four separate sub-systems described together only to the extent that there is some synergy between the sub-systems. The four separate sub-systems include (1) an admit system, (2) a diagnostic/prescription system, (3) an event verification system and (4) an event update system.

I. Preferred Embodiment

Referring again to FIG. 1, according to this first preferred embodiment of the invention, an electronic identification device 26 is provided to every patient admitted into a medical facility. In this embodiment device 26 is used with each of the four separate sub-systems and therefore is described generically here prior to description of the four separate sub-systems. Generally, the exemplary device 26 illustrated includes two separate components, a bracelet 16 and a transceiver 17. Bracelet 16 is preferably formed of a tear resistant plastic material and has first and second ends 42, 44, respectively. A clasp 46 is integrally connected to first end 42 and is constructed so that the clasp 46 can receive second end 44 and lock second end 44 relative to first end 42 forming a loop or ring as illustrated. To this end, it should be noted that any mechanism for securing ends 42 and 44 together is suitable. For example, the ends may be secured via adhesive, melting, crimping, etc.

Bracelet 16 forms an identification surface 48. It is contemplated that basic identification information including a patient's name, an identification number and primary appearance characteristics (e.g. height, weight, hair color, etc.) would be printed on identification surface 48. In addition, bracelet 16 includes a transceiver coupling section 50 for coupling transceiver 17 to bracelet 16. Although section 50 may be formed to permanently couple transceiver 17 to bracelet 16, preferably section 50 and transceiver 16 are formed such that transceiver 17 can be removed from section 50 for use with more than a single bracelet. To this end, although not illustrated, a silicon memory wafer might be implanted in identification surface 48 adjacent section 50 which, when transceiver 17 is secured to section 50, can be accessed by transceiver 17 for identification purposes.

Figure 2:
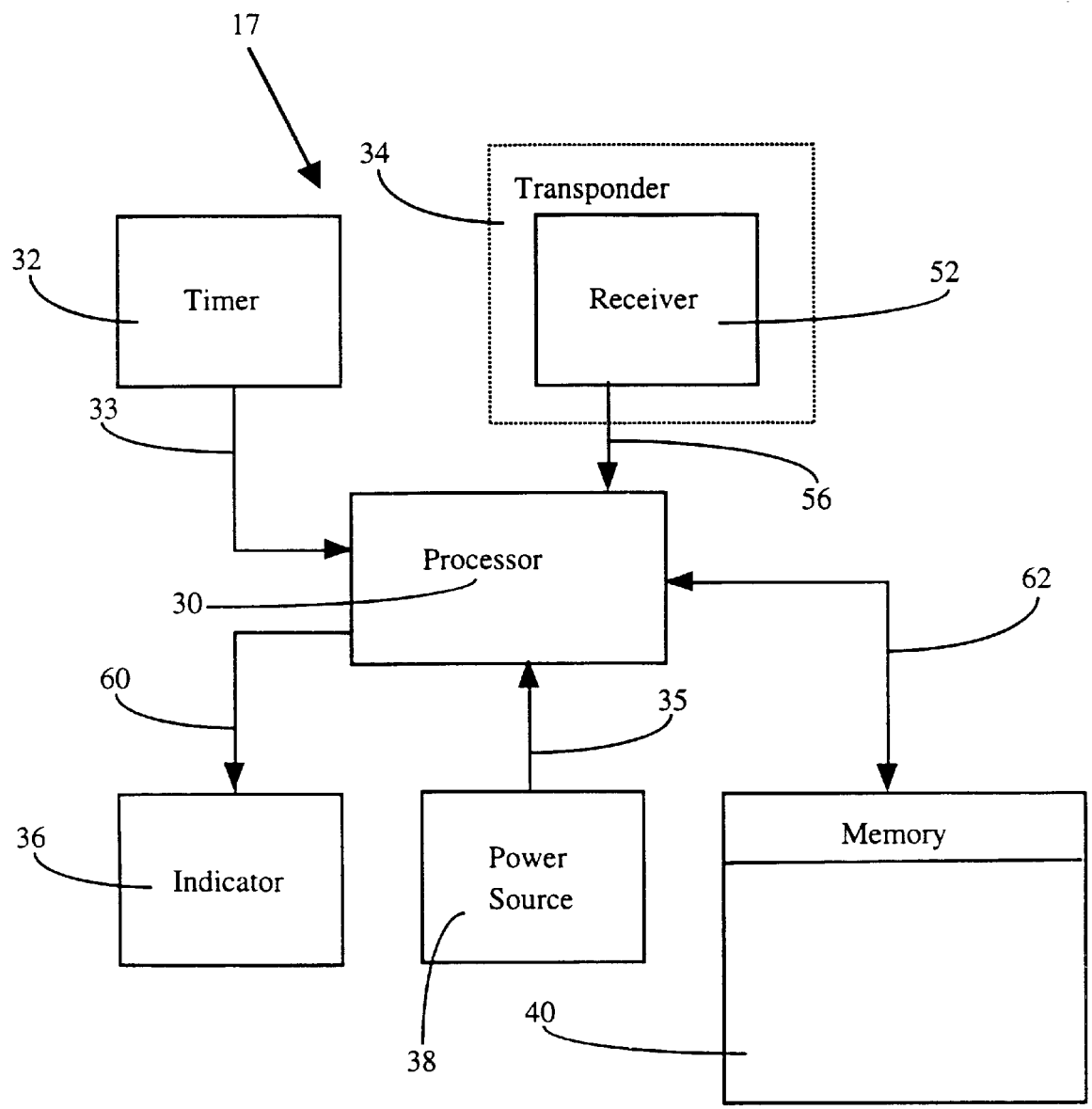
FIG. 2 is a schematic diagram illustrating various components of the identification device of FIG. 1.

Referring now to FIGS. 1 and 2, transceiver 17 includes a processor 30, a timer 32, a transponder 34, an indicator 36 and a power source 38. Source 38 can be any type of power source but is preferably a battery which is linked via a line 35 to processor 30 to provide power thereto. Timer 32 is linked to processor 30 via a data line 33 for providing a timing signal thereto.

In this embodiment transponder 34 includes only a receiver 52. Receiver 52 is constructed such that it can receive information from any of several different external sources via infra-red transmission signals. Receiver 52 is linked via a data line 56 to processor 30, receiver 52 providing received data to processor 30.

Indicator 36 is linked to processor 30 via a one way data line 60 by which processor 30 can provide an indication signal or indication data to indicator 36. It is contemplated that indicator 36 may take any of several different forms depending on the type of functionality required of device 17. For example, indicator 36 may be as simple as a visual alarm (e.g. a diode) which can indicate only two states including an on state and an off state. Indicator 36 may also be an audible tone generator. In the alternative indicator 36 may by a digital scrolling readout which can indicate more detailed information as will be explained in more detail below. Moreover, indicator 36 may be a transmitter for transmitting infra red signals to some external device which can indicate device 26 status.

Processor 30 is a typical silicon based micro-chip processor which receives power from source 38, receives timing signals from timer 32, receives information from transponder 34, can access, manipulate and modify information stored in a memory and can provide indication signals to indicator 36.

As indicated above, transceiver 17 may also include an integral memory 40 or, in the alternative, memory 40 may be provided as an integral part of bracelet 16 which is linkable to processor 30 when transceiver 17 is secured to bracelet 16. In either case, when transceiver 17 is secured to bracelet 16, memory 40 is linked via a two way data bus 62 for information exchange between processor 30 and memory 40. Thus, processor 30 can access, manipulate and modify data stored in memory 40.

Figure 3:
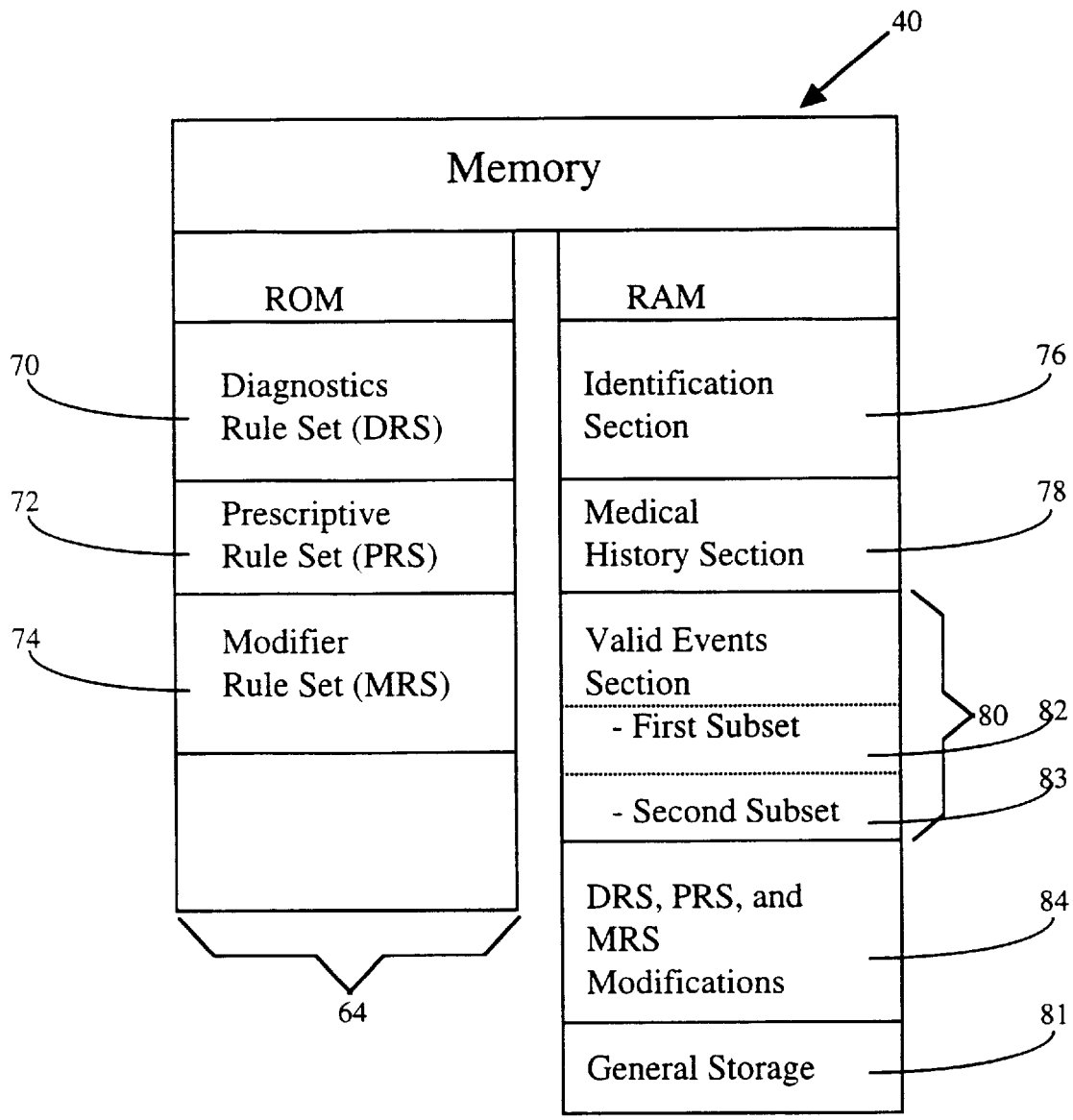
FIG. 3 is a schematic diagram illustrating the various sections of the memory of FIG. 2.

Referring to FIGS. 2 and 3, memory 40 preferably includes both a read only section ROM 64 including data which cannot be modified and a random access section RAM 66 including memory space which can be filled with changeable information. ROM 64 is further dividable into three separate sections, each section including a separate rule set and hereinafter referred to by its respective rule set name. The three rule sets are a diagnostic rule set (DRS) 70, a prescriptive rule set (PRS) 72 and a modifier rule set (MRS) 74.

It is envisioned that DRS 70 will include literally thousands (and perhaps many more as technology permits) of diagnostic rules for diagnosing patient ailment, each rule including a set of factors and a set of diagnoses. For example, an exemplary rule might be:

If:

DRS 1

(1) symptoms A, B and C exist;
(2) patient is female;
(3) 62 or older;
(4) had radiation therapy within last three years;
(5) is on P and Q drugs where Q drug dose is greater than 0.3 mg/hr; and
(6) had heart pains in last 4 months;

then diagnosis may be D1 or D8. Here there are six factors and two possible diagnoses.

Another rule might be:

If:

DRS 2

(1) symptoms A, B, X and Y;
(2) patient 50 or older; and
(3) past addiction to alcohol;

then diagnosis may be D3, D4 or D8. Here there are three factors and three possible diagnoses.

Similarly, it is envisioned that PRS 72 will include thousands of prescriptive rules for prescribing cures for patient diagnosis. For example, an exemplary rule might be:

If:

PRS 1

(1) diagnosis is D1;
(2) patient is female;
(3) is on and Q drugs where Q drug dose is greater than 2 mg/hr;
(4) had radiation therapy in last 2 days;

then prescription is P1 and P4 in M and N doses, respectively; but:

(5) if no radiation therapy in last two days:

then prescription is P1 and P8 in E and F doses, respectively.

It is also envisioned that MRS 74 will have literally thousands of modifier rules used to modify sections of RAM 66 as a function of changing medical history. For example, assuming drug X has been prescribed for a patient to take every four hours, every day for two weeks. Also assume that drug X should not be taken within 24 hours of a PET scan event being performed. In this case, an exemplary modifier rule might be:

If:

MRS 1

(1) PET scan within previous 24 hours; and
(2) on drug X;

then change prescription to drug Y for remaining portion of 24 hour period following PET scan.

RAM 66 also includes several different sections earmarked for storage of different types of data. The different RAM sections include an identification section 76, a medical history section 78, a valid events section 80, a DRS, PRS and MRS modifications section 84 and a general storage section 81. Identification section 76 includes information required to identify a patient typically comprising the patient's name, social security number, a patient ID number, age, weight, height, hair and eye color, etc. For the purposes of this explanation the most important information in section 76 is some terse patient identification information such as the patient ID number.

It is contemplated that medical history section 78 includes information indicating a complete medical history for a specific patient. The complete medical history will typically include patient age, sex, nationality, allergies, blood type, present weight, historical weight information (e.g. weight changes throughout patient's life), present medical conditions including symptoms, historical medical conditions (e.g. conditions throughout patient's life), present addictions, past addictions, past drug use, both prescribed and not prescribed, current drug use, therapeutic history and current status, historical medical procedures performed on the patient, allergies, observed effects of previously prescribed therapy, drugs, procedures, parent's medical histories and perhaps other types of information including hobbies, travels, eating habits, supplements taken, exercise routines, employment, family information (e.g. marital status, number of children if any), exposure to different sicknesses and diseases, etc. In addition, it is envisioned that section 78 will identify times and dates of all medical, diagnostic and therapeutic events in a patient's life, including an indication of the physician who prescribed the event and the physician who administered the event and that section 78 will be updated every time either a medical event is performed, an event is prescribed or some other noteworthy change occurs in a patient's medical condition or history which might affect subsequent diagnosis and prescription. In effect, section 78 is a comprehensive personal history indicating any factor which may be considered important from a diagnostic and prescriptive perspective.

Valid events section 80 includes all medical, therapeutic and diagnostic events which have been prescribed by a physician for a specific patient. For example, a valid events section may include the following:

(1) between 9:00 AM and 9:30 AM May 15, 1998, administer 2.0 mg drug X and 1.0 mg drug Y;

(2) between 1:00 PM and 1:30 PM May 15, 1998, administer 2.0 mg drug X;

(3) between 2:00 PM and 3:00 PM May 15, 1998, perform PET scan on lower abdominal;

(4) between 5:00 PM and 5:30 PM May 15, 1998, administer 2.0 mg drug X and 1.0 mg drug Y;

(5) anesthetize patient 4:45 AM May 16, 1998;

(6) surgery on left knee 5:00 AM May 16, 1998;

(7) 2.0 hours after surgery administer 5.0 mg drug B. VE 1

Preferably section 80 is divided into two separate sections including a first sub-set 82 including events which were prescribed and should be performed in the present time period and a second subset 83 including events which were prescribed but are to be performed during some period other than the present period. For example, referring to the list of valid events VE 1 above, on May 15, 1998 between 9:00 and 9:30 AM only event (1) should be performed and therefore only event (1) is in first subset 82 at that time, all events thereafter being in second subset 83. As will be explained in more detail below, after an event has been performed, performance of the event is noted in medical history section 78 and the event is deleted from section 80.

Modifications section 84 includes either additional diagnostic, prescriptive or modifier rules to be appended to the DRS, PRS or MRS, respectively, includes new diagnostic, prescriptive or modifier rules to replace some of the rules in sets 70, 72, or 74, or includes additional factors to be used to modify one of sets DRS 70, PRS 72 or MRS74. For example, referring again to DRS 1 above, research may have shown that the diagnosis indicated has been prevalent in females 50 years or older rendering the third factor (ie. (3) 62 or older) incorrect. In this case, because ROM 64 cannot be modified, modifications section 84 can be used to correct the factor so that factor (3) is instead "50 or older". In addition, if a new diagnosis is identified based on several different factors, an entirely new diagnostic rule may be provided.

General storage section 81 is used by processor 30 to manipulate various types of data and information as will be described in more detail below.

Referring still to FIGS. 2 and 3, processor 30 can access all rule sets 70 and 72 to identify rules to be applied when identifying a likely correct diagnosis and a likely correct prescription. In addition, processor 30 can access each of RAM sections 76, 78, 80, 84 and 81 to read all data stored therein, can manipulate data stored therein and can modify data stored therein. Moreover, processor 30 can access MRS 74 and apply the MRS 74 to a medical history after an event has been performed to generate an updated valid event set for a patient.

While the above examples of rules, medical history, valid events and modifications are extremely simple, it should be noted that the present invention contemplates a much more complex system and that the simple examples described above and hereinafter are only used for the sake of simplifying this explanation.

A. Admit System

Referring to FIGS. 1 and 3, when a patient is first admitted to a medical facility, admit system 8 is used in conjunction with device 26 to provide identification information, medical history and previously prescribed valid events to identification section 76, history section 78 and events section 80, respectively. To this end, referring also to FIGS. 4 and 5, admit system 8 includes a computer having a processor 90, a power source 92, a memory 94 and a transmitter 96. Memory 94 is linked to processor 90 via a two way data bus 95. Memory 94 is a RAM for receiving and storing information and providing the information to processor 90 upon command. Power source 92 is linked to processor 90 via a power line 97 and provides power to processor 90. Transmitter 96 is linked to and receives data for transmission from processor 90 via a data bus 93. Transmitter 96, like receiver 52 (see FIG. 2) is preferably an infra red transmitter.

In addition to computer 86, admit system 8 also includes some type of input device 88a or 88b linked to processor 90 for receiving identification, medical history and prescribed events information. The input device may take the form of a keyboard 88a used by facility personnel to manually input required information. However, as required identification, medical history and prescribed events information will often comprise a large amount of information, a keyboard for manual input is not preferred.

Instead, a medical history card reader 88b for downloading a patient's medical history from a card is a preferred input device. Reader 88b is to be used with a patient identification card 98 and includes a slot 99 for receiving card 98. Although not illustrated, card reading components are located inside reader 88b for reading information from an inserted card 98. Reader 88b is linked to processor 90 via a data line. One such medical history card and associated system for reading information from the card is described in U.S. Pat. No. 5,659,741 which is identified in more detail and incorporated by reference above. It is contemplated that at some point nearly every potential patient will carry a medical history card 98 which includes a complete history including, in addition to typical medical history information, patient identification information and current prescribed events information. In this case, during admittance, a patient gives his card to a receptionist and the receptionist inserts the card in slot 99. Reader 88b reads all history information and transfers the information via line 102 and processor 90 to memory 94.

In the alternative, it is contemplated that in the near future patient medical histories will be available on-line via the Internet or some other similar information network. In this case a patient's medical history can be downloaded from the network into memory 94.

A monitor 104 is provided for viewing medical history information and visually confirming that the information read from card 98 or downloaded or manually entered is specific to the patient being admitted. After confirmation that the medical history is specific to the patient being admitted, an identification device 26 is personalized by printing terse identification information (e.g. name, patient ID number, hair and eye color, etc.) on identification surface 48. Personalized device 26 is secured to the patient's wrist by wrapping bracelet 16 around the wrist and securing ends 42 and 44 together via clasp 46.

Figure 4:
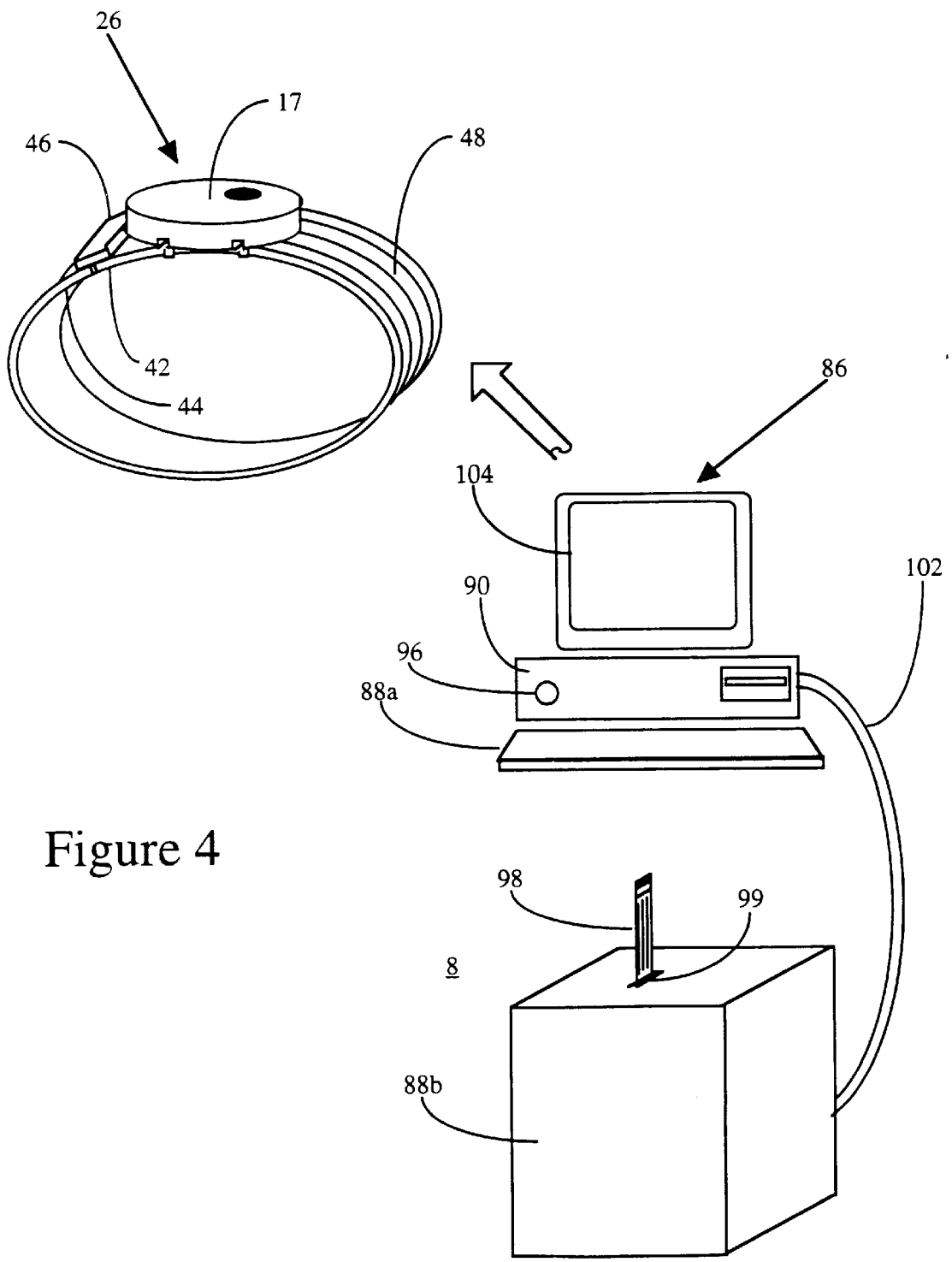
FIG. 4 is a schematic diagram illustrating components of a preferred admit system.
Figure 5:
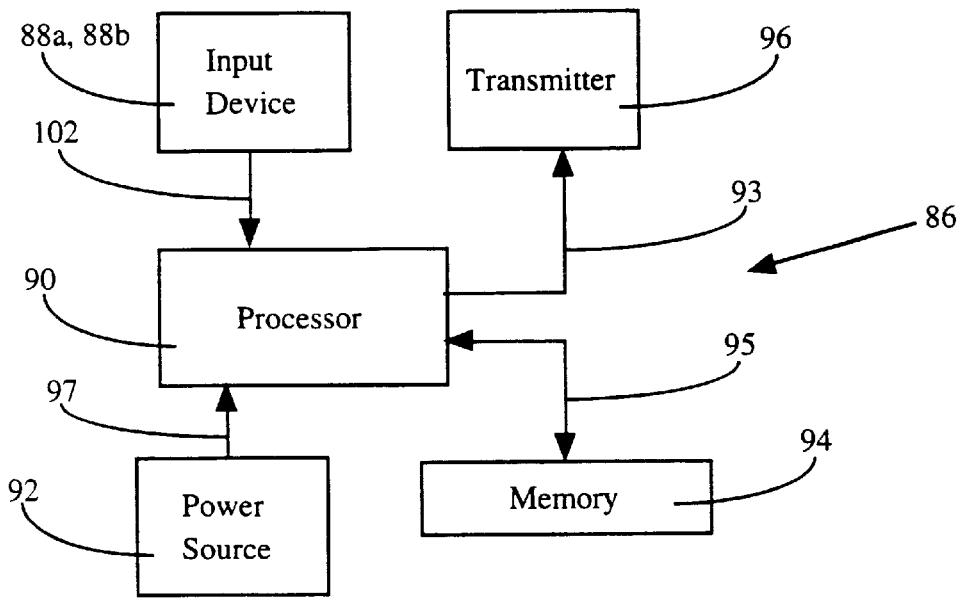
FIG. 5 is a schematic diagram illustrating components of the admit system of FIG. 4.

Next, referring still to FIGS. 4 and 5 and also to FIG. 2, transceiver 17 is placed within close proximity to transmitter 96. Processor 90 accesses the identification, medical history and previously prescribed events information in memory 94 and transmits all of that information via transmitter 96 and infrared red signals to receiver 52.

Receiver 52 receives the transmitted information and provides the information to processor 30. Processor 30 divides the received information into identification information, medical history information and previously prescribed events and, referring again to FIG. 3, stores the divided information in the sections 76, 78 and 80, respectively. In addition, the valid events are also stored in medical history section 78 as they may affect possible future diagnosis and prescription.

In addition, referring still to FIGS. 3 and 5, memory 94 may also be provided with DRS, PRS and MRS modifications for updating the DRS, PRS and MRS in memory 40. In this case, in addition to transmitting identification, history and event information during an admit procedure, the modifications can be transmitted to and received by receiver 52 and thereby by processor 30. Processor 30 recognizes the modifications and stores the modifications in modifications section 84.

B. Diagnostic/Prescription System

Figure 6:
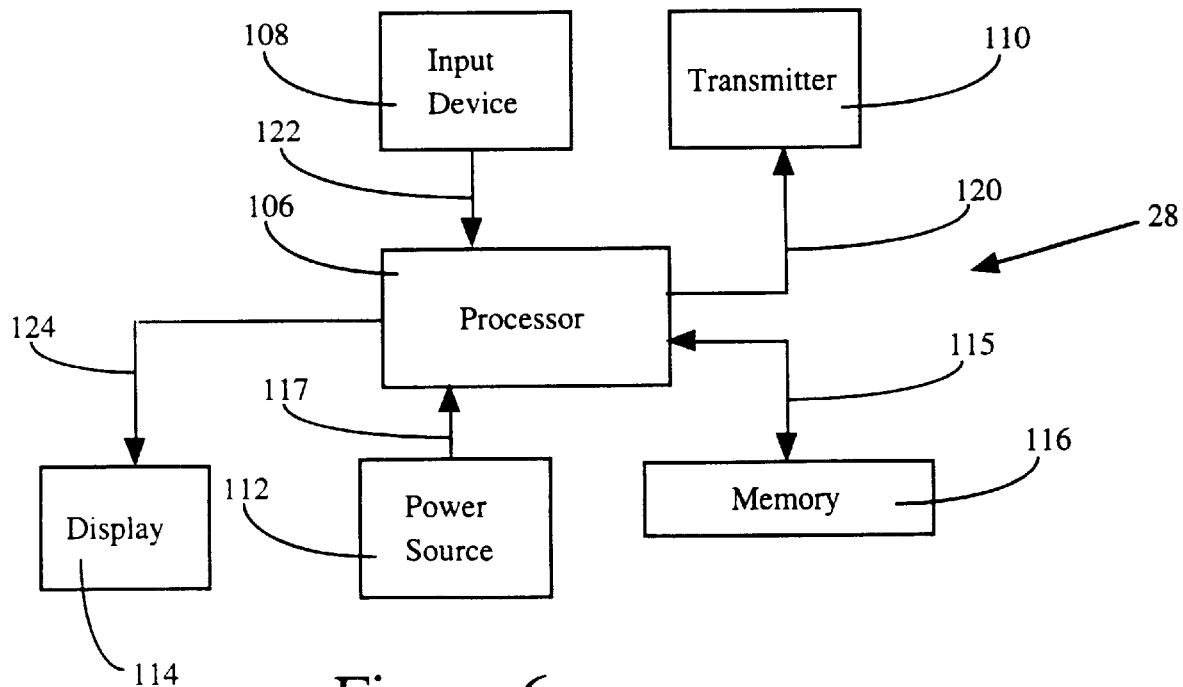
FIG. 6 is a schematic diagram illustrating preferred components of the hand-held programming device of FIG. 1.

Referring to FIGS. 1 and 6, after a patient has been admitted to a medical facility, a physician uses a hand held programing device (HHD) 28 during consultation, examination, diagnosis and prescription. HHD 28 includes a processor 106, a power source 112, a memory 116, a transmitter 110, an input device 108 and a display 114. Memory 116 is linked to processor 106 via a two way data bus 115. Memory 116 is a RAM for receiving and storing information and providing the information to processor 106 upon command. A physician identification code may be provided in memory 116 which indicates the physician who owns the HHD or indicates the physician using the HHD.

Power source 112 is linked to processor 106 via a power line 117 and provides power to processor 106. Transmitter 110 is linked to and receives data for transmission from processor 106 via a data bus 120. Transmitter 110, like receiver 52 (see FIG. 2) is preferably an infra red transmitter. Input device 108, typically a keyboard attached to a flat surface of HHD 28, is linked to processor 106 via a data line 122 and can be used by a physician to input information into memory 116 via processor 106. Display 114 is linked to processor 106 via a data line 124 and is preferably a screen for displaying information as it is entered by the physician.

During an examination, a physician initially consults with a patient to identify any symptoms known to the patient. As the patient identifies symptoms, the physician uses device 108 to input the symptoms into memory 116. To this end, common symptoms may be specified by specific numbers, for example, 1 for soar throat, 2 for nausea, 3 for headache, etc. and a key for specific symptoms may be provided to the physician for identifying the symptoms properly. As the symptoms are entered, entered symptoms are displayed via display 114 for viewing. Where symptoms are entered via a number or similar code, processor 106 may expand the code so that the physician can be sure that correct symptoms are entered. After the initial consultation and entry of known symptoms, the physician can perform a patient examination identifying other symptoms and entering the symptoms into HHD 28 for storage in memory 116.

Given the symptoms identified and entered, the physician forms a diagnosis and enters the diagnosis into HHD 28 which is also stored in memory 116. Then, the physician, based on his experience and the diagnosis, identifies what he believes to be a suitable prescription for the diagnosis and enters the prescription into HHD 28 for storage in memory 116.

When symptoms, diagnosis and prescription are entered into HHD 28, HHD 28 forms a data message string which includes all of the entered data. In addition, HHD 28 may include a data field within the string identifying the physician entering the data.

Referring to FIGS. 2 and 6, once the symptoms, diagnosis and prescription have been entered into memory 116 and all have been checked for accuracy via display 114, the physician places HHD 28 in the vicinity of transceiver 17 and presses a transmit button (not illustrated) on device 108 thereby causing processor 106 and transmitter 110 to transmit the message string to receiver 52.

Figure 7:
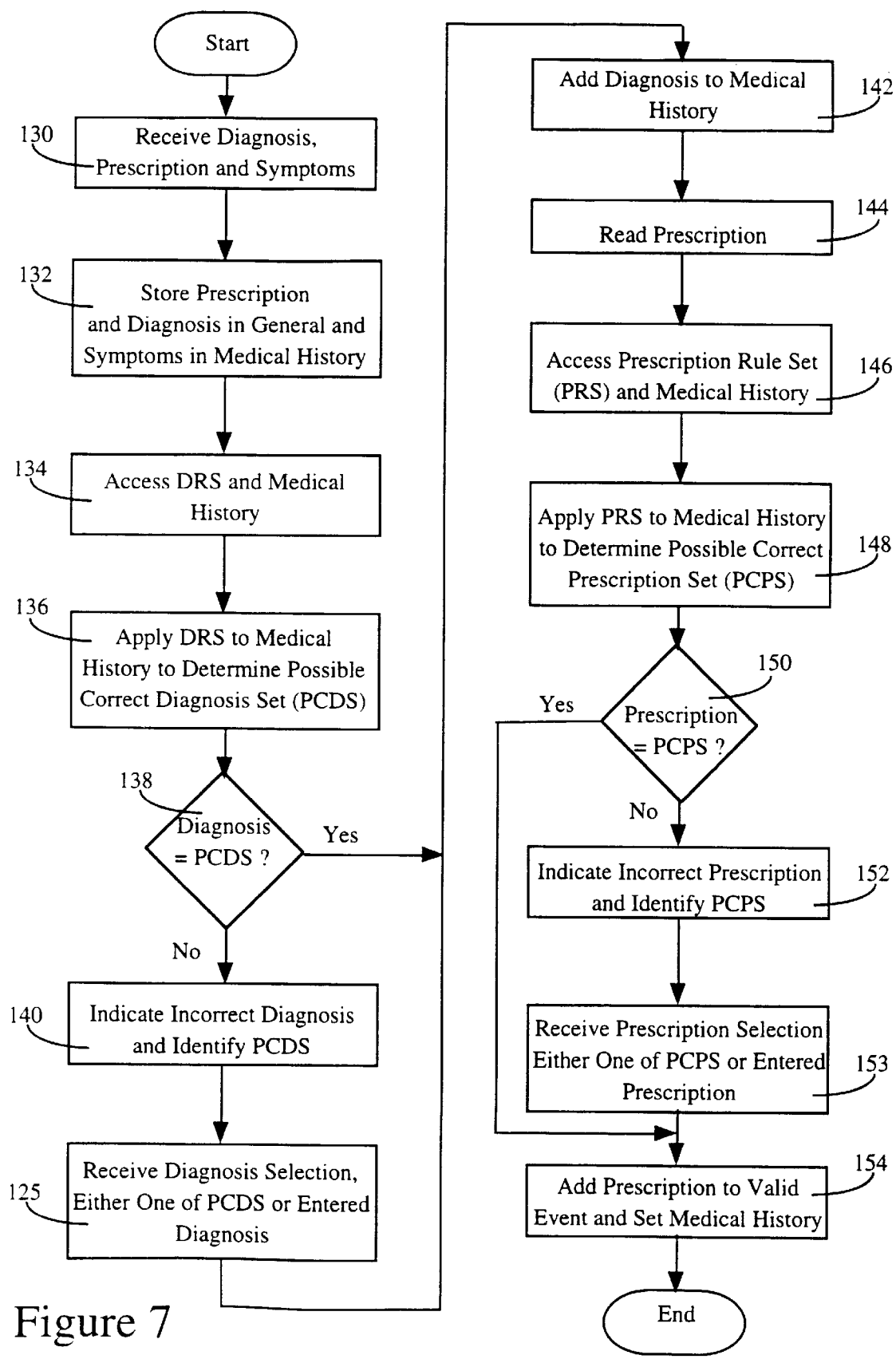
FIG. 7 is a flow chart illustrating a preferred method for identifying incorrect diagnoses and prescriptions.

Referring also to FIG. 7, an exemplary method performed by transceiver 17 when symptom, diagnosis and prescription information is received is illustrated in flow chart form. Beginning at process block 130 the information is received and provided to processor 30. At block 132, processor 30 divides the information into symptoms, diagnosis and prescription and, where provided, physician identifying information. Referring also to FIG. 3, processor 30 stores the symptoms information and the physician identifying information in medical history section 78, and stores the diagnosis and prescription information in storage section 81.

At block 134 processor 30 accesses ROM 64 and specifically DRS 70 and also accesses patient medical history section 78. At block 136 processor 30 applies DRS 70 to the medical history to determine all different diagnosis which may in fact be correct and thereby creates a possible correct diagnosis set (PCDS). To this end, in addition to considering all of the symptoms entered by the physician via HHD 28 which have been stored as part of the patient's medical history in section 78, processor 30 considers all other factors in the patient's medical history. Thus, while a specific diagnosis might be suitable for specific symptoms in a 20 year old relatively healthy male, the same diagnosis might not be suitable for a 20 year old female or a 65 year old male or a 20 year old male who has other non-obvious conditions in addition to the specific symptoms. By considering the complete medical history more suitable and perhaps the most suitable diagnosis will be provided more often.

At decision block 138 processor 30 compares the diagnosis to the PCDS to determine if the diagnosis is a possible diagnosis. Where the diagnosis entered by the physician is not a possible diagnosis (i.e. is not in the PCDS), at block 140 processor 30 indicates via indicator 36 that the diagnosis is likely incorrect. In addition, where indicator 36 is a display, processor 30 can identify the PCDS so that the physician can quickly identify a more likely diagnosis. Preferably, display indicator 36 displays the PCDS and the previously entered diagnosis as an additional, although unlikely option. Then, the physician can reuse HHD 28 to select one of the PCDS diagnosis or again select one of the PCDS diagnosis which is then transmitted to receiver 52. At block 125 the selected diagnosis is received. At block 138, if the diagnosis entered is part of the PCDS, processor control passes to block 142.

At block 142, processor 30 stores the entered or selected diagnosis in medical history section 78. At process block 144, processor 30 accesses general storage and reads the prescription entered by the physician. At block 146 processor 30 accesses PRS 72 and again accesses medical history section 78 to identify the medical history. At block 148 processor 30 applies PRS 72 to the medical history (which now also includes the entered diagnosis) and thereby determines every possible correct prescription given the updated state of the medical history thereby generating a possible correct prescription set (PCPS). To this end, in addition to considering the diagnosis entered by the physician via HHD 38 which has been stored as part of the patient's medical history in section 78, processor 30 considers all other factors in the patient's medical history. Thus, while a specific prescription might be suitable for a diagnosis A in a 20 year old relatively healthy male, the same prescription might not be suitable for a 20 year old female or a 65 year old male or a twenty year old male who has other non-obvious conditions. By considering the complete medical history more suitable and perhaps the most suitable prescriptions will be prescribed more often.

At decision block 150, processor 30 compares the entered prescription to the PCPS to determine if the entered prescription is a possible correct prescription. Where the prescription entered by the physician is not a possible correct prescription, at block 152 processor 30 indicates via indicator 36 that the prescription is likely incorrect. In addition, where indicator 36 is a display, processor 30 can identify the PCPS so that the physician can quickly identify a more likely or more accurate prescription. Preferably, display indicator 36 displays the PCPS and the previously entered prescription as an addition, although unlikely option. Then, the physician can reuse the HHD 28 to select one of the PCPS prescriptions or again select the previously entered prescription which is then transmitted to receiver 52. At block 153 the selected prescription is received.

At block 154, if the prescription entered is part of the PCPS or if the physician reselected the previously selected prescription, processor 30 adds the prescription to the valid events section 80 with a time stamp indicating the period during which the event should be performed. In the event that the prescription is a multiple event such as ingestion of medicine every four hours or radiation therapy every 24 hours, each event in the multiple events is stored in section 80 as a separate event with its own time stamp.

In the event that more than one event has been prescribed for a patient, the process illustrated in FIG. 7 can be performed twice. At the end of the first performance, assuming that the first prescription is part of the PCPS or is reselected, the first prescription is added to valid events section 80 and is also added to medical history section 78. During the second performance of the method of FIG. 7, at step 146 the first prescription is part of medical history section 78 and is therefore used to determine if the second prescription is a possible correct prescription at decision block 150.

C. Event Verification System

Referring again to FIG. 1, prior to using any medical device (e.g. machine or apparatus) to perform an event on a patient, according to the present invention, a specifying device is used in conjunction with identification device 26 to determine if the event to be performed was prescribed, in which case the event would be a valid event. To this end, referring again to FIG. 6, a physician's HHD 28 can be used to specify an event to be performed, hereinafter referred to as a specified event (SE). Using input device 108, the physician can identify a specified event which processor 106 stores in memory 116. Once again, to streamline event entry common events may be given a number code such as 1 for administration of drug A, 2 for administration of drug B, 3 for a CAT scan and so on. Processor 106 can display specified events for confirmation via display 114 as they are entered.

Figure 8:
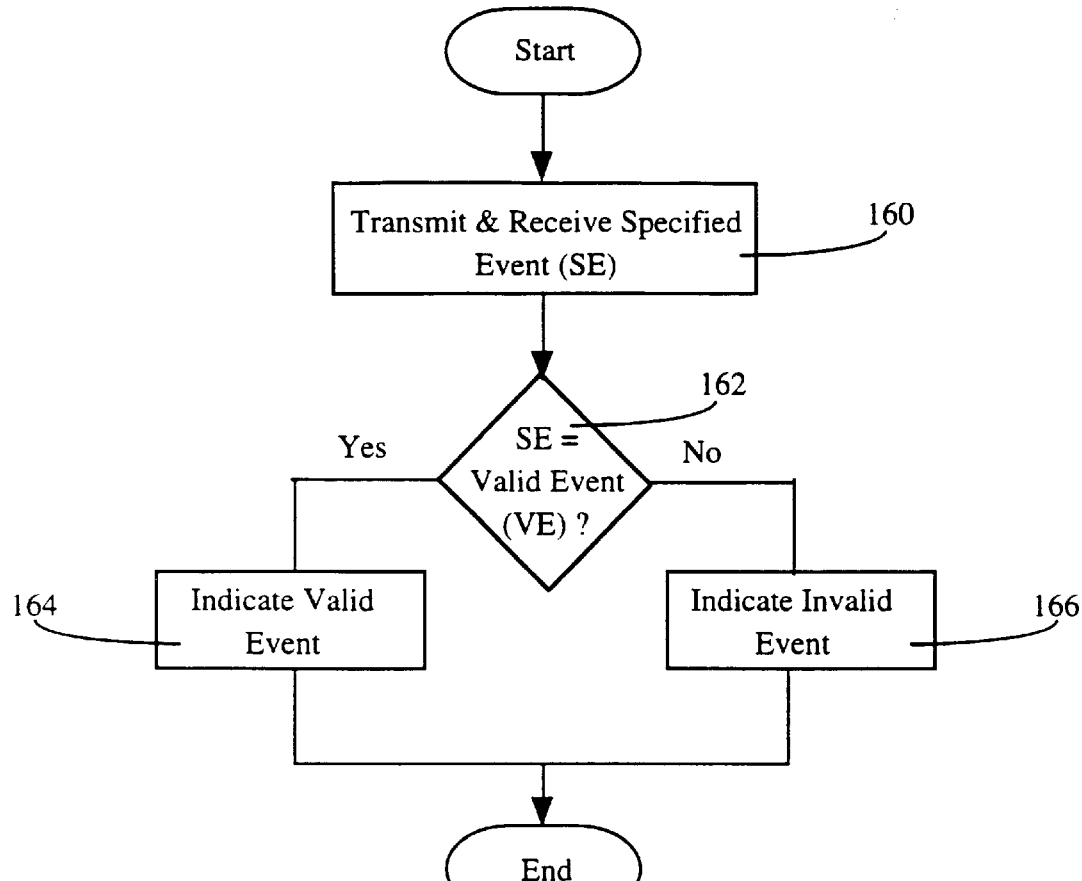
FIG. 8 is a flow chart illustrating a method for identifying valid and invalid medical events prior to performing those events on a patient.

Referring to FIG. 8, a preferred method of determining if a specified event was prescribed prior to performing the event is illustrated in flow chart form. Referring also to FIGS. 2 and 6, after an event to be performed has been entered into HHD 28, HHD 28 forms another data message string indicating the specified event and which may identify the specifying physician in a separate field. Just prior to performing the specified event, at process block 160, the physician can place HHD 28 in proximity of identification device 26 and press a button (not illustrated) on HHD 28 thereby transmitting an initial signal via transmitter 110 to receiver 52. In this embodiment the initial signal is preferably the message string indicating the specified event SE and, where provided, the physician identifying information.

When the initial signal is received via receiver 52, processor 30 separates the specified event SE from the physician identifying information. In addition, processor 30 may access timer 32 and time stamp the SE with the current time. The current time usually will be required for comparison to the valid events (VE) as many VEs will be time specific.

At block 162 processor 30 compares the time stamped SE to the VEs to determine if the SE is a VE. Where the specified event SE is not a valid event VE, at block 164 processor 30 indicates via indicator 36 that the specified event is not a valid event. Where the specified event is a valid event, at block 166 processor 30 indicates so via indicator 36 and stores the specified event, including the physician identifying information, in the patient's medical history section of memory 40.

Assuming that the specified event SE is a valid event VE, a physician can proceed to perform the specified event SE and can then use HHD 28 to update both medical history section 78 and valid events section 80. To this end, the HHD can be used to transmit a specified event complete signal to receiver 52. When the event complete signal is received, processor 30 indicates completion of the event in medical events section 78 and deletes the specified event from valid events section 80 thereby indicating that the completed event is no longer a valid event.

Where the specified event is not a valid event VE, the physician may or may not elect to perform the specified event after an independent judgement concerning the prudence of performing the event. Where the specified event is performed despite not having been earlier prescribed, after performance, the physician should again use HHD 28 to update medical history section 78 to indicate that the event has been performed. To aid the physician in determining if the specified event should be performed even if not earlier prescribed, the physician may use HHD 28 in conjunction with device 26 to form a diagnosis and identify a prescription which device 26 can double check to ensure suitability in the manner described above with respect to the diagnosis/prescription sub-system.

According to a second variation of this first preferred embodiment, all medical devices (e.g. machines and apparatuses) in a medical facility which can perform any medical, therapeutic or diagnostic event on a patient may be provided with the capability to specify the event which the specific device can perform. For example, referring again to FIG. 1, according to this second variation of the first preferred embodiment, MRI system 10 is a system capable of indicating an MRI as a specified event to be performed. Similarly, CAT scan system 12 is a "smart" system capable of indicating a CAT scan as a specified event to be performed. Similarly, each of systems and apparatuses 14, 18, 20, 22 and 24 are all "smart" systems and apparatuses capable of specifying the events each of those systems and apparatuses perform, respectively.

For the purposes of this explanation any device which specifies an event to be performed will be referred to herein as a specifying device. In addition, to simplify this explanation, the invention will be described in the context of only a single specifying "smart" device, IV apparatus 22, although the discussion hereinafter is applicable to any of the systems, machines and/or apparatuses (e.g. 10, 12, 14, 18, 20, 22, or 24) in FIG. 1.

Figure 9:
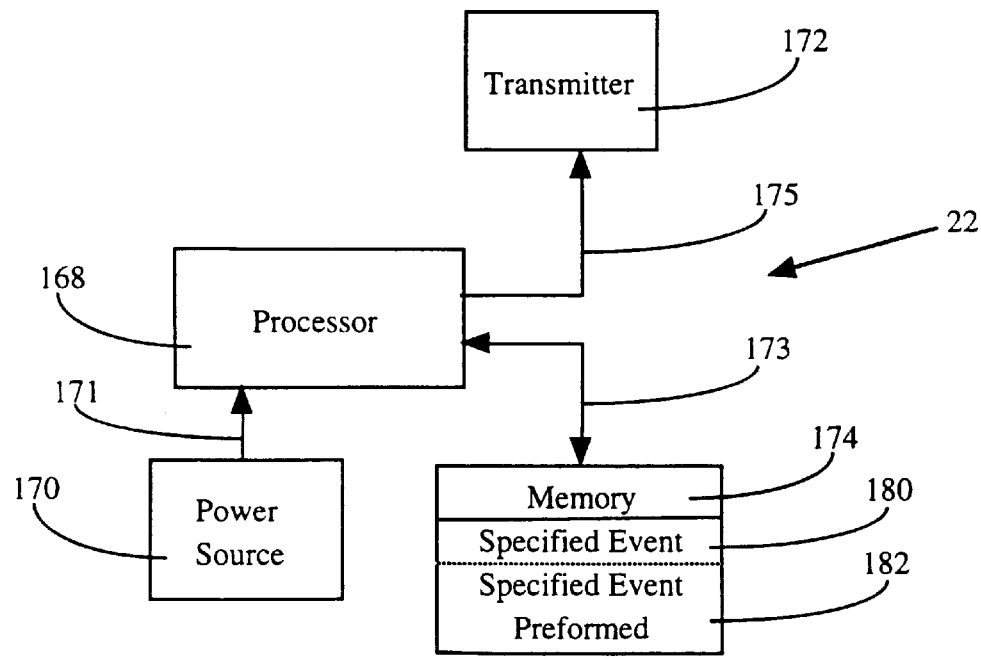
FIG. 9 is a schematic diagram illustrating components of a specifying device.

Referring to FIGS. 1 and 9, IV apparatus 22 includes a processor 168, a power source 170, a transmitter 172 and a memory 174. Source 170 is linked to processor 168 via a power line 171 and supplies power thereto. Where apparatus 22 needs to be mobile, source 170 may be a rechargeable battery. A data bus 173 links memory 174 to processor 168 so that data stored in memory 174 can be down loaded to processor 168 on command. Transmitter 172 is linked to processor 168 via a data line 175 for receiving data to be transmitted therefrom. Memory 174 only contains two segments of data, a first segment 180 indicating a specified event which apparatus 22 performs and a second segment 182 indicating that the event specified by first segment 180 has been performed. In this case, apparatus 22 is an IV apparatus and therefore the specified event is dispersion of a drug having a specific potency. For the purposes of this explanation it will be assumed that the drug in IV apparatus 22 is drug X having a potency of 2 mg/liter. In this case, the specified event might be dispersion of drug X (2 mg/liter) at the rate of 0.1 liters/hour. In addition, the specified event may also indicate the patient on which the event should be performed.

In operation, prior to linking IV apparatus 22 to a patient, apparatus 22 is placed in close proximity to device 26 and either a physician can press a button (not illustrated) on apparatus 22 causing processor 168 to transmit the specified event in memory 174 or apparatus 22 can automatically transmit the specified event (e.g. apparatus 22 may transmit the specified event periodically). In any event, the specified event is transmitted to processor 30 which performs the method illustrated in FIG. 8 to determine if the specified event is a valid event. Assuming the specified event is invalid processor 30 and indicator 36 cooperate to indicate that the specified event is invalid at which point the physician can determine if the specified event should be performed despite not being a valid event.

Referring again to FIG. 9, second data storage segment 182 is used to implement the event update feature described below.

D. Event Update System

Figure 10:
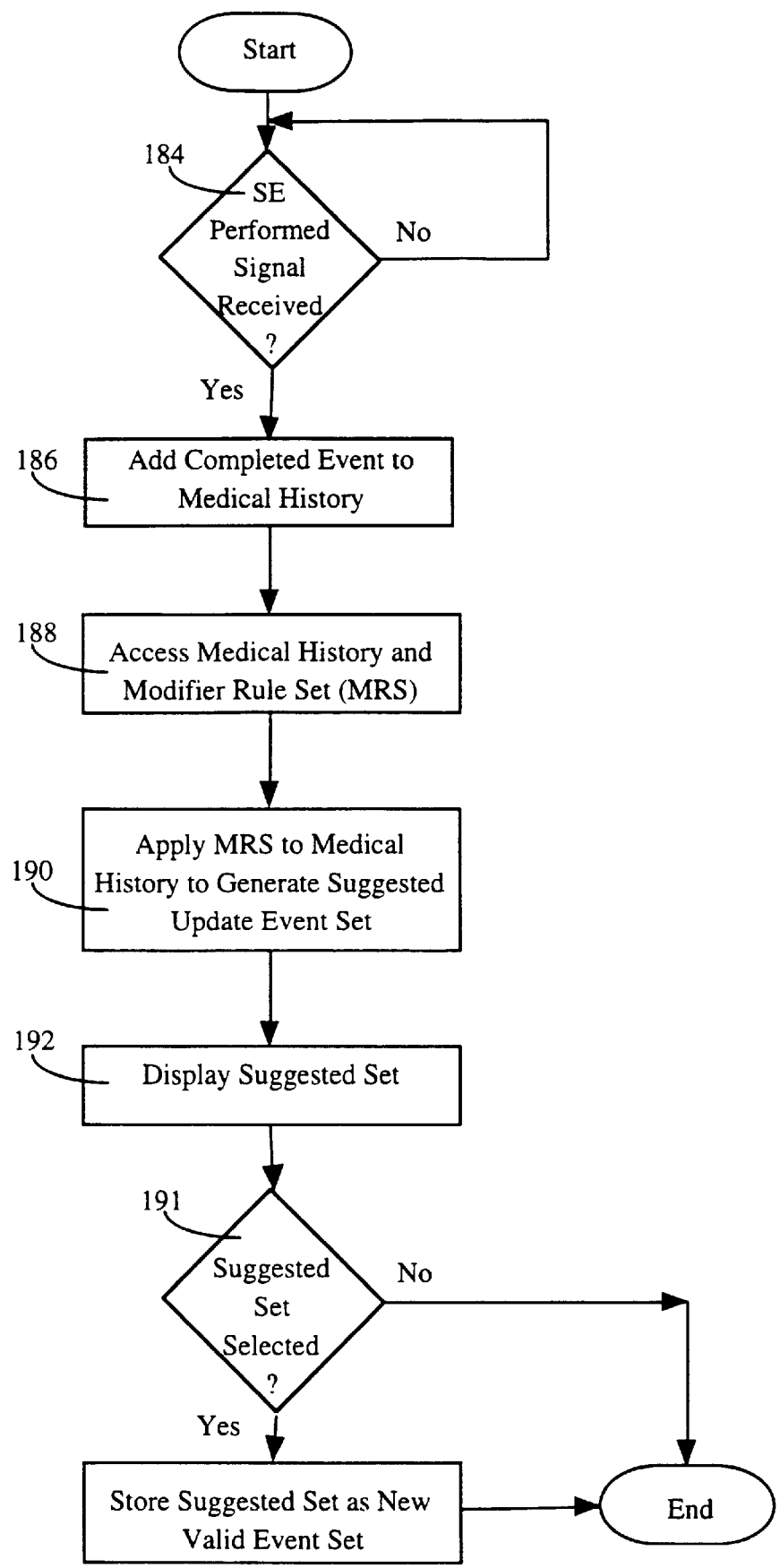
FIG. 10 is a flow chart illustrating a method for updating a valid event section of the memory illustrated in FIG. 3.

Referring now to FIG. 10, a preferred method for automatically updating a medical history section 78 and suggesting changes to a corresponding valid events section 80 after an event has been performed is illustrated in flow chart form. Referring also to FIGS. 1, 2, 3 and 9, any time IV apparatus 22 performs an event on a patient regardless of whether the event was previously specified or not, during performance of the event processor 168 monitors performance of the event. Once the specified event has been completely performed, processor 168 accesses data from second segment 182 of memory 174 and transmits a specified event performed signal via transmitter 172 to receiver 52.

In FIG. 10, at decision block 184, processor 30 monitors received signals to identify a signal indicating that the specified event has been performed. Until the performed sinal is received, processor 30 remains in a loop. Once the performed signal is received, at block 186 processor 30 adds the completed or performed specified event to medical history section 78 and, assuming the performed event was part of the valid event set, deletes the performed specified event from the valid event set.

At process block 188, processor 30 accesses the MRS 74 and medical history section 78 and at block 190, processor 30 applies the MRS to the medical history (including the recently performed specified event), to generate a suggested updated valid event set. To this end, in many cases the suggested set will be identical to the initial valid event set as performance of the specified event will not appreciably effect other prescribed events. However, in some cases performance of one event will appreciably effect a patient's immediate or long term conditions such that events which were valid prior to the performed specified event are no longer necessary or may in fact be harmful to a patient.

For example, where a drug was being provided to maintain a regular size gall bladder, if the gall bladder is removed during a specified and performed event, thereafter the drug for maintaining regular gall bladder size would no longer be needed. As another example, assume that two drugs X and Y are both suitable for treating a diagnosis Q but that generally drug X causes better results. In addition, assume that while drug X generally has better results than drug Y, for 24 hours after a radiation therapy session drug X should not be used because it will cause adverse side effects. In this case, assuming a patient is on drug X and a specified and performed event is a radiation therapy session. After the session is completed, the MRS would change the prescription of X to Y for the next 24 hours.

The suggested updated valid events set is displayed for viewing at block 192 via indicator 36. In addition, event set changes should be highlighted in some way to enable a physician to easily identify changes. Next, the physician can use HHD 28 to either select the suggested set or to indicate that no changes should be made to the valid event set, sending an appropriate signal indicating his selection to receiver 52 which receives the signal at decision block 191 where the selection is identified.

Regardless of whether or not a physician elects to modify the valid events set, when HHD 28 is used to make the election, the HHD 28 also transmits physician identifying information to device 26 so that a log of the decision and who made the decision can be formed.

If the physician elects to accept the suggested set (including valid event set changes), at block 187 processor 30 correlates the physician identifying information with the suggested set and stores the suggested set and correlated information as the new valid event set. In the alternative, where the physician elects not to accept the suggested set, the decision not to elect the suggested set is documented, the physician identifying information is correlated with the decision and the decision and identifying information is stored in the patient's medical history section without changing the valid events set.

II. Other Preferred Embodiments

Referring again to FIG. 1, while a first preferred embodiment of the present invention is described above, clearly the present invention contemplates many other embodiments for admittance, diagnosis/prescription, event verification and event updating. For example, instead of having a complex transceiver 17 which requires a relatively large memory section to store all required data and rule sets (see FIG. 3) and a relatively simple HHD 28 or specifying device, the invention could be implemented using a relatively simple identification device 26 and more complex "other" devices. The more complex "other" devices may include a more complex HHD 28 and specifying devices separately or in combination with a more complex central computer system.

Figure 11:
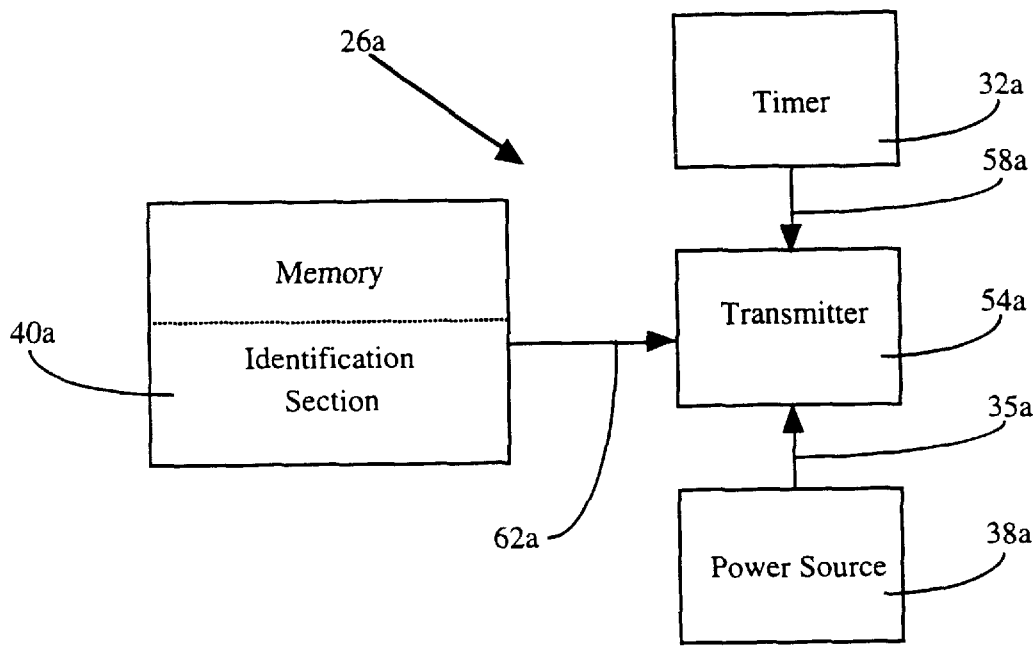
FIG. 11 is a schematic diagram illustrating components of a second embodiment of an identification device.

To this end, referring to FIG. 11, a second and simpler identification device 26a may simply include a timer 32a, a power source 38a, a memory 40a and a transmitter 54a. In this case, source 38a is linked to transmitter 54a via a power line 35a, timer 32a is linked via data line 58a and memory 40a is linked to transmitter 54a via a one way data bus 62a. Memory 40a includes only a single segment specifying a patient identification.

Figure 12:
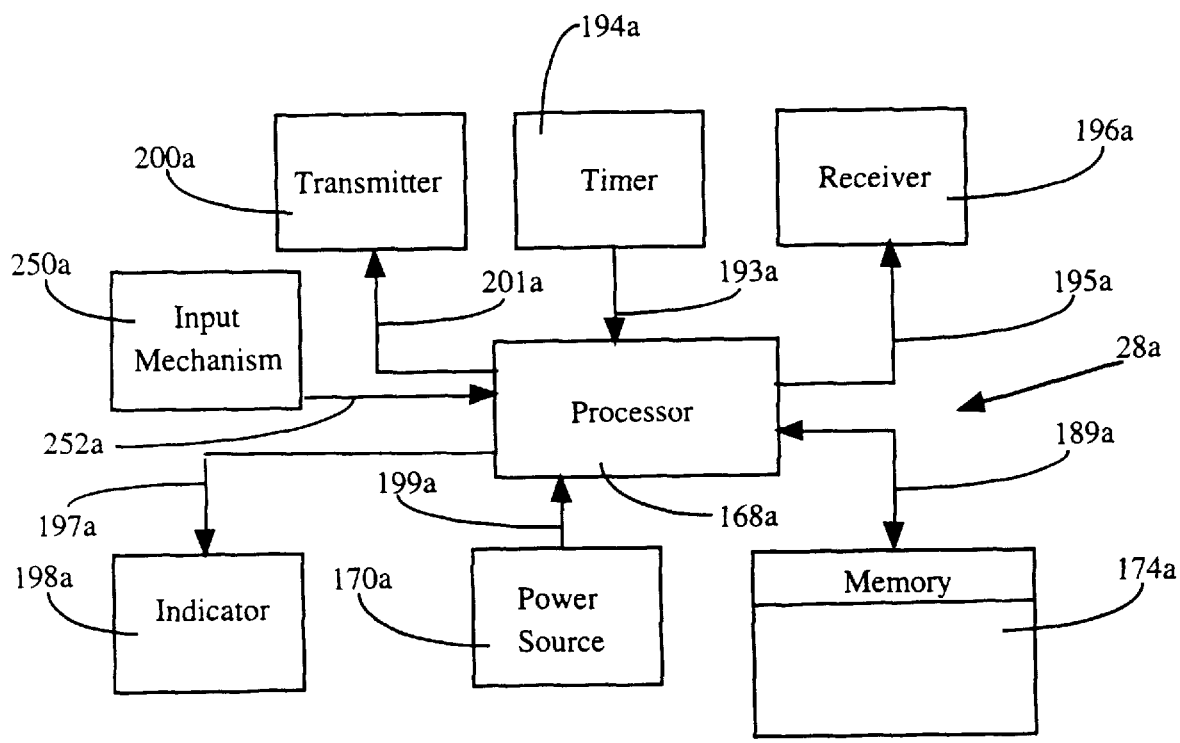
FIG. 12 is a schematic diagram illustrating components of a second embodiment of a specifying device.

Referring also to FIG. 12, a second and more complex HHD is illustrated. HHD 28a includes a processor 168a, a timer 194a, a receiver 196a, a power source 170a, an indicator 198a, a memory 174a, a transmitter 200a and an input mechanism 250a (e.g. a keyboard). Timer 194a is linked to processor 168a, via a timing line 193a, receiver 196a is linked to processor 168a via a data line 195a, indicator 198a is preferably a display screen and is linked to processor 168a via a data line 197a, source 170a is linked to and provides power to processor 168a via a power line 199a, memory 174a is linked to processor 168a via a two way bus 189a, transmitter 200a is linked via line 201a and mechanism 250a is linked via line 252a. In this embodiment the diagnostic rule set DRS and prescriptive rule set PRS are stored by HHD 28a in memory 174a (note these rule sets are not patient specific and therefore are always stored in the HHD memory).

Figure 13:
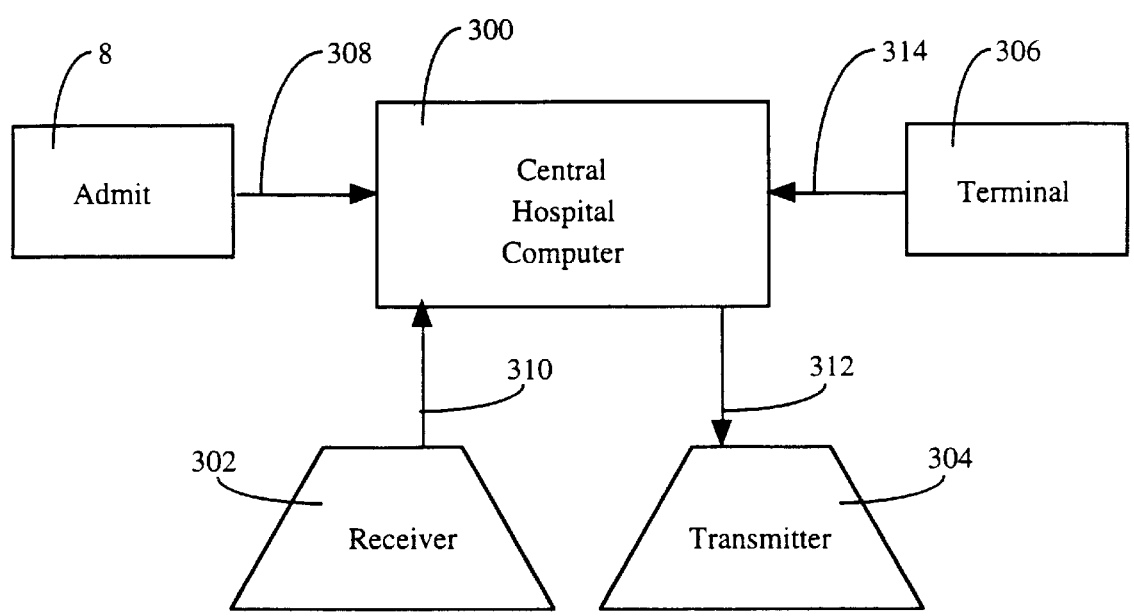
FIG. 13 is a schematic diagram illustrating components of a central hospital computer system.

Moreover, referring to FIG. 13, a central hospital computer 300 is provided which is linked to an admit system 8 (see again FIGS. 4 and 5), a receiver 302, a transmitter 304 and an interface terminal 306 via lines 308, 310, 312 and 314, respectively. Although not illustrated, in this embodiment computer 300 includes a RAM for storing various types of modifiable data, a programmable read only memory PROM and a processor which generally performs only two functions. First, the central computer processor controls data routing and organization as computer 300 operates as a central data storage device for all patient information. Second, the central computer processor operates to update valid events as events are performed on a patient. To this end computer 300 PROM includes the modifier rule set MRS used to modify valid events when a specified event has occurred.

In this embodiment, as with the first embodiment described above, during an admittance procedure a patient identification number is provided for the patient and patient information is again entered into a hospital computer system via a patient medical history card in conjunction with system 8. System 8 correlates the patient identification number with the patient's medical history and valid (i.e. previously prescribed) events. In this embodiment, instead of storing the patient medical history information on device 26a, that information is stored in computer 300 which is accessible by HHD 28a (or any other smart medical device for that matter). In addition valid events are correlated with the patient identification number and stored via computer 300 for access by HHD 28a.

An identification device 26a is provided for the patient including at least some terse patient identification information printed on the bracelet portion and the patient identification number stored in memory 40a.

After admittance, when a physician enters an examination room to perform an examination, after a friendly greeting, the physician positions HHD 28a adjacent device 26a to receive an identification signal generated by device 26a. This can be accomplished in one of two ways. First, if device 26a is equipped with an activation button (not illustrated), when the button is pressed, transmitter 54a transmits the patient identification number via rf or the like in the direction of HHD 28a. In the alternative, device 26a can be programmed such that timer 32a causes transmitter 54a to periodically transmit an extremely low power identification signal which can only be detected by a receiving device which is proximate device 26a.

In either case, when HHD 28a receives the identification signal, HHD 28a accesses central computer 300 and provides the identification number to the computer 300. Computer 300 then compares the received identification number with all identification numbers in its memory. When a matching identification number is identified, computer 300 accesses the medical history and valid events which correlate to the identified number and provides the medical history and valid events information to HHD 28a.

Preferably, HHD 28a and central computer 300 communicate via rf or the like, HHD 28a transmitting the patient identification number to computer 300 via transmitter 200a and computer 300 receiving the number via receiver 302. In the alternative, transmitter 200a might also be a hardwire or telephone line hookup to receiver 302 to minimize rf signals in the hospital environment. The medical history and valid events are then transmitted to HHD 28a and are stored in memory 174a.

Next, as in the first embodiment, the physician performs an examination identifying symptoms and enters the symptoms into HHD 28a via mechanism 250a which are stored as part of the medical history. Then, based on the symptoms, the physician identifies a likely diagnosis and enters the diagnosis in HHD 28a.

As the physician forms the diagnosis, HHD 28a applies diagnosis rule set DRS to the medical history to determine a possible correct diagnosis set PCDS. When the physician's diagnosis is entered, HHD 28a compares the physician's diagnosis to the PCDS and either indicates a match or provides additional possible diagnosis which account for all factors in the patient's medical history. Once a diagnosis is finally selected the selected diagnosis is added to the patient's medical history in memory 174*a*.

Next, the physician identifies a prescription to treat the diagnosis and enters the prescription into HHD 28*a*. As the physician identifies a likely correct prescription, HHD 28*a* is identifying a possible correct prescription set PCPS based on the diagnosis and all other medical history factors by applying the prescription rule set. After the physician enters the prescription HHD 28*a* compares the prescription to the PCPS and either indicates a match or provides other more likely prescriptions. The physician makes the final prescription selection via HHD 28*a* and the final prescription is added to the patient's medical history and to the valid events in memory 174*a*.

After diagnosis and prescription are complete, the modified patient medical history and valid events in memory 174*a* are downloaded to central computer 300 for storage and later access. To this end, the physician can either immediately download the updated information via transmitter 200*a* and receiver 302 or, at a later time (e.g. after the physician's rounds are completed) can transmit the information. Downloaded updated information is earmarked by the patient identification number. When computer 300 receives updated information computer 300 identifies the patient number and either replaces the old information with new information or simply updates the old information with the changes made by the physician.

Referring again to FIG. 12, in addition to HHD 28*a* having the components identified, according to this second embodiment other "smart" medical devices will also have the components identified which can be used to verify valid events prior to performing the events and which can update medical history and valid events based on performed events. To this end, during the remainder of this explanation it will be assumed that device 28*a* is an IV instead of an HHD.

As in the first embodiment it is contemplated that prior to using any medical device to perform an event on a patient, the inventive system is used to ensure that the event to be performed is a valid event (i.e. was actually prescribed and is to be performed at the specific time in question).

Referring again to FIGS. 11 and 12, assuming IV 28*a* is to be connected to a patient to distribute a specific drug, prior to connecting IV 28*a* to the patient, input mechanism 250*a* is used to specify what drug is to be provided to the patient, what the drug dose will be and the time at which the drug is to be administered. If IV processor 168*a* includes a clock, the clock can indicate the present time as the time to start administration. The drug, dose and time are all part of the specified event SE to be performed by IV 28*a*.

Next, IV 28*a* is positioned adjacent the patient. Device 26*a* transmits the patient identification number signal to IV receiver 196*a*. In the alternative, if IV 28*a* cannot be positioned adjacent the patient, an HHD or some other suitable electronic device equipped to receive and transmit data could be used to gather information from bracelet 26*a*, transport the data to a location adjacent IV 28*a* and retransmit the data to IV 28*a*. Referring also to FIG. 13, when the number signal is received, IV 28*a*, like the HHD prior to diagnosis, provides the signal to central computer 300 which correlates the signal with one of the identification numbers in its memory. When a matching number is identified, computer 300 correlates the patient number with valid events for the patient and provides a valid events list to IV 28*a* via transmitter 304 and receiver 196*a*.

IV 28*a* receives the valid events VE and stores the events in memory 174*a*. Next, IV processor 168*a* compares the specified event SE to each valid event VE in the valid events list. Where the SE matches one of the VEs, IV 28*a* indicates a match via indicator 198*a*. When a match is indicated the attending physician can proceed to hook up the IV 28*a* to the patient and carry out the SE.

However, when the SE does not match one of the VEs, IV 28*a* indicates an invalid event via indicator 198*a*. Thereafter IV 28*a* will not allow the SE to be performed until the attending physician makes an independent additional judgement to administer the SE and affirmatively overrides the IV 28*a*.

Assuming the SE is performed, during performance IV 28*a* tracks drug administration and forms a log which is stored in memory 174*a* as a medical history update record. After SE performance, IV 28*a* provides the medical history update record to computer 300 which is added to the patient's medical history.

Optionally, when a medical history record is added to the medical history by computer 300, computer 300 accesses the modifier rule set MRS and applies the MRS to the modified medical history to determine if any changes should be made to the valid events list for the patient. If no changes should be made, after the updated medical history record is stored computer 300 may either indicate that no changes are to be made (via terminal 306) or may do nothing. However, if computer 300 determines that a change in the valid events list should likely be made, the computer 300 can indicate possible changes to be made to a physician and indicate why the change should be made via terminal 306. For example, computer 300 can identify the performed SE, the MRS rule applied in determining that a change should be made and the medical history factors which were considered in identifying the likely change. Then, using terminal 306, the physician can determine if a change should be made to the events list or if the list should remain unchanged and can cause changes accordingly.

In this example, the IV 28*a* may be provided with the patient's ID number via computer 300 or manual entry. In this case, when IV 28*a* receives the patient ID number, IV 28*a* can compare the received number to the number earlier provided to determine if the event to be performed by the IV was in fact specified for the particular patient.

According to yet a third preferred embodiment of the present invention, instead of providing either a complex identification device as in the first embodiment or a complex HHD and "smart" medical devices as in the second embodiment, a more complex central hospital computer could be provided to carry out diagnostics, prescription, validation and event updating. In this case, the identification device, HHD and medical devices would operate simply as input and output devices for the central computer, providing the patient identification number, physician diagnosis and prescription information and specified event information to the computer and receiving indicating signals from the computer related to diagnosis, prescription, valid and invalid events and suggestions on how to modify diagnosis, prescription and valid event lists.

It should be understood that the methods and apparatuses described above are only exemplary and do not limit the scope of the invention, and that various modifications could be made by those skilled in the art that would fall under the scope of the invention. For example, each of the three embodiments described above distributes processing power differently. While each embodiment has certain unique advantages, the invention is meant to cover other configurations which distribute processing in a different manner. For example, an identification device may apply the diagnostic rule set DRS and the prescriptive rule set PRS while an HHD or central computer applies the modifier rule set MRS. In addition, any of the identification device, HHD, smart machines or central computer may include one or more different types of indicators for indicating valid or invalid events, diagnosis and prescription suggestions and event update suggestions.

Moreover, while certain data and information has been described above as being stored in RAM and other in ROM or PROM, clearly the invention is not so limited and any data could be stored in RAM, ROM or PROM.

Furthermore, where a central computer performs some or essentially all of the data and information processing, the central computer and other intermediate devices can be thought of as a single specifying device cooperating with the identification device to carry out the procedures described above.

Moreover, in any embodiment the patient identification number which is correlated with a patient's valid event list might be a first patient identification number and an event specifying device may be provided with a second patient identification number which indicates the specific patient for which the event is being specified. In this case, instead of comparing the specified event to a valid event list, system devices could cooperate to compare the first and second patient identification numbers. Where the numbers match, the system indicates a match. Where the numbers do not match the system could either indicate a mismatch or perform additional comparison of the specified event to the valid events list.

Clearly other forms of hand shaking and communication between the identification and specifying devices are contemplated by the present invention. For example, a specified event may be transmitted twice to ensure proper transmission and reception. In addition, other data transfer could be transmitted and received twice. In the alternative, when data is received it cold be transmitted back to the initially transmitting device for validation. Also, although preferred data transfer occurs through rf transmission and reception, other forms of transfer including hard wire and other wireless medium are contemplated.

In addition, while the identification device is described as including a wristband for securing the device to a patient's limb, the device could take some other embodiment such as a badge or a pin. Moreover, the identification device power source may take some other form such as an antenna which receives energy when placed within a varying electromagnetic field. In this case the HHD and other devices would have to provide a field for communicating with the identification device.

To apprise the public of the scope of this invention, I make the following claims.

I claim:

1. A system for identifying medical events which have not been prescribed prior to performing the events on a patient, the system comprising:

an identification device associated with a first patient, the identification device including a power source, a comparison device processor, a memory and a transponder linked to the source for power and linked to the memory to read data stored in the memory the transponder including a receiver, the memory including a patient specific valid events section which includes a list of valid events which have been prescribed for the first patient; and at least one specifying device including a power source and a transponder linked to the source for power, the specifying device transponder including a transmitter, the specifying device specifying a procedure to be performed on a patient, the procedure being a specified event;

wherein, one of the identification device and the specifying device includes an indicator; and wherein, to initiate an identification process, the transmitter transmits an initial signal which is received by the receiver and, after the initial signal is received and during the identification process, the processor compares the specified event to the list of valid events and wherein, when the specified event is not a valid event, the processor causes the indicator to indicate that the specified event is an invalid event.

2. The system of claim 1 wherein the specifying device includes a specifying device memory and a processor linked to the specifying device memory to access data stored in the specifying device memory.

3. The system of claim 1 wherein the identification device also includes the indicator.

4. The system of claim 3, wherein the indicator includes an alarm.

5. The system of claim 3, wherein the initial signal specifies the specified event.

6. The system of claim 3, wherein the specifying device also includes an indicator, when the identification device identifies an invalid event, the identification device transmits an invalid event signal to the specifying device receiver and, when the invalid event signal is received, the specifying device indicates an invalid event.

7. The system of claim 1 wherein the identification device is the first device and the identification device memory includes a patient identification section including patient ID data for identifying the patient.

8. The system of claim 1 for use with a medical apparatus for performing the specified event, the system also for preventing invalid events, the specifying device processor linked to the medical apparatus for disabling the apparatus when the specified event is invalid, and, when the indicator indicates that the specified event is an invalid event, the specifying device processor disables the medical apparatus.

9. The system of claim 8, wherein the specifying device is a part of the medical apparatus.

10. The system of claim 1 for use with a medical apparatus for performing the specified event, one of the system devices being an updating device which communicates with the medical apparatus, the system also for identifying an updated set of valid events after a specified event has been performed after an event has been performed, the updating device determining that the event has been performed and identifying the updated valid event set as a function of performance of the specified event.

11. The system of claim 10, wherein the updating device memory includes a modifier rule set indicating how the valid events should be modified as a function of various factors including at least performance of the specified event, the updating device using the modifier rule set to identify the updated valid event set after performance of the specified event.

12. The system of claim 10, wherein the specifying device is a part of the medical apparatus.

13. The system of claim 1 wherein the valid events may include medications, diagnostic procedures, therapeutic procedures and medical procedures.

14. The system of claim 1 wherein the identification device also includes a fastener configured to attach the identification device to the patient.

15. The system of claim 14 wherein the fastener includes a band which is securable around a patient's limb.

16. The system of claim 1 wherein the indicator can indicate invalid events and valid events and, when a specified event is a valid event, the indicator specifies a valid event.

17. The system of claim 16, wherein valid events include prescribed events, a first subset of valid events being prescribed events to be performed within a present time period, a second subset of valid events being prescribed events to be performed within a time period other than the present period, the identification device including a clock linked to the comparison device processor and separating valid events into first subset events and second subset events and comparing the specified event each of the first subset and second subset events, the indicator indicating if the specified event is a first subset or a second subset event.

18. The system of claim 17, wherein, when a specified event is a second subset event, the indicator also indicates that the specified event is an invalid event.

19. The system of claim 1 wherein the identification device power source is a battery.

20. The system of claim 1 wherein the identification power source is an antenna which receives energy when placed within a varying electromagnetic field.

21. The system of claim 1 wherein the valid events list is correlated with a first patient identification number, the specified event is correlated with a second patient identification number, each of the first and second patient identification numbers is a patient number, the initial signal includes one of the patient numbers and the processor compares the specified event to the valid event list by comparing the first and second patient identification numbers.

22. The system of claim 1 wherein the specifying event requires a physician to provide physician identifying information prior to specifying an event and wherein the processor forms a log indicating specified events correlated with specifying physician identifying information.

23. A method for use with a medical apparatus for performing a specified event, for identifying medical procedures which can be performed on a patient and for preventing invalid events, the method to be used with a system including an identification device associated with a first patient, a specifying device and a medical apparatus, each of the identification and specifying devices being system devices, one of the system devices being a comparison device, the comparison device having a patient specific valid events section which includes a list of all valid events which may be performed on the first patient, the specifying device processor linked to the medical apparatus for disabling the apparatus when the specified event is invalid, the method including the steps of:

specifying a specified event which is a procedure to be performed on a patient;

comparing the specified event to the valid events for the first patient to determine if the specified event is a valid event; and if the specified event is not a valid event, disabling the medical apparatus.

24. The method of claim 23, for use with a medical apparatus for performing the specified event, the method also for identifying an updated valid event set after a specified event has been performed the method further including the steps of, determining when an event has been performed and identifying an updated valid event set reflecting performance of the specified event.

25. The method of claim 24, wherein the step of modifying includes the step of, identifying a modifier rule set which indicates how the valid events should be modified as a function of various factors including at least performance of the specified event and applying the modifier rule set to modify the valid events.

26. A system for identifying medical events which have not been prescribed prior to performing the events on a patient and for preventing invalid events form occurring, the system to be used with a medical apparatus for performing specified events, the system comprising:

an identification device associated with a first patient, the identification device including a power source, a memory and a transponder linked to the source for power and linked to the memory to read data stored in the memory; and at least one specifying device including a power source, a specifying device processor and a transponder linked to the source for power, the specifying device specifying a procedure to be performed on a patient, the procedure being a specified event, each of the identification and specifying devices being system devices, the specifying device processor linked to the medical apparatus for disabling the apparatus when the specified event is invalid;

wherein, a first system device transponder includes a transmitter and a second system device transponder includes a receiver;

wherein, one of the system devices is a comparison device including a memory and a comparison processor linked to the comparison device memory, the comparison device memory including a patient specific valid events section which includes a list of all valid events which have been prescribed for the first patient and may be performed on the first patient; and wherein, to initiate an identification process, the transmitter transmits an initial signal which is received by the receiver and, after the initial signal is received and during the identification process, the comparison processor compares the specified event to the list of valid events which may be performed on the first patient and wherein, when the specified event is not a valid event, the specifying device processor disables the medical apparatus.

27. The system of claim 26, wherein the specifying device is the comparison device and the identification device is the first device, the identification device memory including a patient identification section including patient ID data identifying the patient, and, wherein, the initial signal includes the patient ID data.

28. The system of claim 26 wherein the specifying device is a part of the medical apparatus.

29. The system of claim 26 wherein at least one of the system devices includes an indicator and, when the medical apparatus is disabled, the indicator indicates an invalid event.

30. A system for use with a medical apparatus for performing a specified event, for identifying medical events which have not been prescribed prior to performing the events on a patient and for identifying an updated set of valid events after a specified event has been performed, the system comprising:

an identification device associated with a first patient, the identification device including a power source, a memory and a transponder linked to the source for power and linked to the memory to read data stored in the memory; and at least one specifying device including a power source and a transponder linked to the source for power, the specifying device specifying a procedure to be performed on a patient, the procedure being a specified event, each of the identification and specifying devices being system devices;

wherein, a first system device transponder includes a transmitter and a second system device transponder includes a receiver;

wherein one of the system devices includes an indicator;

wherein, one of the system devices is a comparison device including a memory and a processor linked to the comparison device memory, the comparison device memory including a patient specific valid events section which includes a list of all valid events which have been prescribed for the first patient;

wherein, to initiate an identification process, the transmitter transmits an initial signal which is received by the receiver and, after the initial signal is received and during the identification process, the processor compares the specified event to the list of valid events which may be performed on the first patient and wherein, when the specified event is not a valid event, the processor causes the indicator to indicate that the specified event is an invalid event; and wherein one of the system devices is an updating device which communicates with the medical apparatus, the updating device determining that the event has been performed and identifying the updated valid event set as a function of performance of the specified event.

31. The system of claim 30, wherein the updating device memory includes a modifier rule set indicating how the valid events should be modified as a function of various factors including at least performance of the specified event, the updating device using the modifier rule set to identify the updated valid event set after performance of the specified event.

32. The system of claim 30, wherein the specifying device is a part of the medical apparatus.

33. The system of claim 30, wherein the identification device is the first device.

34. The system of claim 33, wherein the identification device transponder also includes a receiver and the specifying device transponder also includes a transmitter.

35. The system of claim 30, wherein the specifying device is the first device.

36. The system of claim 35, wherein the identification device includes the indicator.

37. A system for identifying medical events which have not been prescribed prior to performing the events on a patient, the system comprising:

an identification device associated with a first patient, the identification device including a power source, a memory and a transponder linked to the source for power and linked to the memory to read data stored in the memory; and at least one specifying device including a power source and a transponder linked to the source for power, the specifying device specifying a procedure to be performed on a patient, the procedure being a specified event, each of the identification and specifying devices being system devices;

wherein, a first system device transponder includes a transmitter and a second system device transponder includes a receiver;

wherein, one of the system devices includes an indicator which can indicate invalid events and valid events;

wherein, one of the system devices is a comparison device including a memory, a processor linked to the comparison device memory and a clock linked to the comparison device processor, the comparison device memory including a patient specific valid events section which includes a list of all valid events which have been prescribed for the first patient and may be performed on the first patient, a first subset of valid events being prescribed events to be performed within a present time period, a second subset of valid events being prescribed events to be performed within a time period other than the present period; and wherein, to initiate an identification process, the transmitter transmits an initial signal which is received by the receiver and, after the initial signal is received and during the identification process, the comparison device processor compares the specified event to the list of valid events which may be performed on the first patient and wherein, when the specified event is not a valid event, the processor causes the indicator to indicate that the specified event is an invalid event and, when a specified event is a valid event, determining if the specified event is a first subset or a second subset event and causing the indicator to if the specified event is a first subset or a second subset event.

38. The system of claim 37, wherein, when a specified event is a second subset event, the indicator also indicates that the specified event is an invalid event.

39. The method of claim 23, wherein the step of specifying includes the step of transmitting an initial signal via a first of the system devices and receiving the initial signal via a second of the system devices.

40. A system for controlling enablement of a medical apparatus, the apparatus for performing a procedure, the system comprising:

an identification device associated with a first patient, the identification device including a power source, a memory and a transponder linked to the source for power and linked to the memory to read data stored in the memory, the memory including a patient specific first ID number; and at least one specifying device including a power source, a memory and a transponder linked to the source for power and to the memory, the specifying device also linked to the medical apparatus for controlling enablement thereof, the specifying device memory including a second patient ID number that indicates a patient for which the medical procedure is to be performed, each of the identification and specifying devices being system devices;

wherein a first system device transponder includes a transmitter and a second system device transponder includes a receive;

wherein, one of the system devices is a comparison device including a memory and a processor linked to the comparison device memory; and wherein, to control enablement of the medical apparatus, the transmitter transmits one of the patient ID numbers which is received by the receiver and, after the transmitted patient ID number is received and during an identification process, the processor compares the first and second patient ID numbers and wherein, when the first and second patient ID numbers are different, the specifying device disables the medical apparatus.

* * * * *